(12) United States Patent
Meng et al.

(10) Patent No.: US 8,901,142 B2
(45) Date of Patent: Dec. 2, 2014

(54) FUSED TRICYCLIC COMPOUNDS AS MTOR INHIBITORS

(75) Inventors: Zhaoyang Meng, Lansdale, PA (US); M. Arshad Siddiqui, Newton, MA (US); Panduranga Adulla P. Reddy, Walpole, MA (US); Mehul F. Patel, Willow Grove, PA (US); Yang Nan, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/234,837

(22) PCT Filed: Jul. 20, 2012

(86) PCT No.: PCT/US2012/047529
§ 371 (c)(1),
(2), (4) Date: Jan. 24, 2014

(87) PCT Pub. No.: WO2013/016164
PCT Pub. Date: Jan. 31, 2013

(65) Prior Publication Data
US 2014/0171456 A1 Jun. 19, 2014

Related U.S. Application Data

(60) Provisional application No. 61/511,607, filed on Jul. 26, 2011.

(51) Int. Cl.
*A61K 31/519* (2006.01)
*C07D 487/14* (2006.01)
*C07D 519/00* (2006.01)

(52) U.S. Cl.
CPC ............ *C07D 487/14* (2013.01); *C07D 519/00* (2013.01); *A61K 31/519* (2013.01)
USPC .......................................... 514/267; 544/251

(58) Field of Classification Search
USPC .......................................... 514/267; 544/251
See application file for complete search history.

(56) References Cited

FOREIGN PATENT DOCUMENTS

WO WO2010118207 10/2010

OTHER PUBLICATIONS

Schenone, ATP—Competitive Inhibitors of mTOR: An Update, Current Medicinal Chemistry, Jul. 11, 2011, 2995-3014, 18.

*Primary Examiner* — Jeffrey H Murray
*Assistant Examiner* — Oluwafemi Masha
(74) *Attorney, Agent, or Firm* — Richard S. Parr; Laura M. Ginkel

(57) ABSTRACT

The present invention relates to certain pyrazolo[1,5-a]pyrrolo[3,2-e]pyrimidine and dipyrazolopyrimidine compounds of Formula (I) as inhibitors of mammalian Target Of Rapamycin (mTOR) kinase, which is also known as FRAP, RAFT, RAPT or SEP. The compounds may be used in the treatment of cancer and other disorders where mTOR is deregulated. The present invention further provides pharmaceutical compositions comprising the pyrazolo[1,5-a]pyrrolo[3,2-e]pyrimidine or dipyrazolopyrimidine compounds.

13 Claims, No Drawings

FUSED TRICYCLIC COMPOUNDS AS MTOR INHIBITORS

FIELD OF THE INVENTION

This invention is directed to certain pyrazolo[1,5-a]pyrrolo[3,2-e]pyrimidine and dipyrazolopyrimidine compounds of Formula (I) as inhibitors of mammalian Target Of Rapamycin (mTOR) kinase, which is also known as FRAP, RAFT, RAPT or SEP. The compounds may be useful in the treatment of cancer and other disorders where mTOR is deregulated.

BACKGROUND OF THE INVENTION

The mammalian target of rapamycin (mTOR) is a central regulator of cell growth and proliferation and plays a gatekeeper role in the control of cell cycle progression. The mTOR signaling pathway, which integrates both extracellular and intracellular signals, is activated in certain cellular processes such as tumor formation, angiogenesis, insulin resistance, adipogenesis, and T-lymphocyte activation. In addition, the mTOR signaling pathway is deregulated in diseases such as cancer and type 2 diabetes. See Laplante et al., J. Cell Science 122, pp 3589-3593 (2009).

mTOR mediates mitogenic signals from PI3K/AKT through to the downstream targets S6K1 (ribosomal S6 kinase 1), 4E-BP1 (eukaryotic translation initiation factor 4E-binding protein) and AKT. Recently, it has been shown that mTOR exists in two complexes. Raptor-mTOR complex (mTORC1) is a rapamycin-sensitive complex that phosphorylates S6K1 and 4E-BP1. Rictor-mTOR complex (mTORC2) is a rapamycin-insensitive complex that phosphorylates AKT at Ser473. Although the precise mechanism by which rapamycin inhibits mTOR function is not well understood, rapamycin partially inhibits mTOR function through mTORC1. Since mTORC2 is involved in the regulation of cell survival, metabolism, proliferation, and cytoskeletal organization in a rapamycin-independent manner, complete inhibition of mTOR function through inhibition of both mTORC1 and mTORC2 may lead to a broader spectrum antitumor activity in the treatment of cancer or better efficacy. In addition, inhibition of both mTORC1 and mTORC2 may lead to better efficacy in treating other diseases than through inhibition of mTORC1 alone.

There exists a need in the art for small-molecule compounds having desirable physicochemical properties that are useful for treating cancer and other disorders associated with deregulated mTOR activity. Specifically, there exists a need for small molecule inhibitors of mTOR kinase that block signaling through mTORC1 and mTORC2 for treating cancer and other disorders.

SUMMARY OF THE INVENTION

The present invention relates to certain pyrazolopyrrolopyrimidine or dipyrazolopyrimidine compounds of Formula (I) as inhibitors of mammalian Target Of Rapamycin (mTOR) kinase, which is also known as FRAP, RAFT, RAPT or SEP. The compounds may be used in the treatment of cancer and other disorders where mTOR is deregulated. The present invention further provides pharmaceutical compositions comprising the pyrazolopyrrolopyrimidine or dipyrazolopyrimidine compounds.

The present invention thus relates to compounds of Formula I and pharmaceutically acceptable salts thereof, as detailed herein:

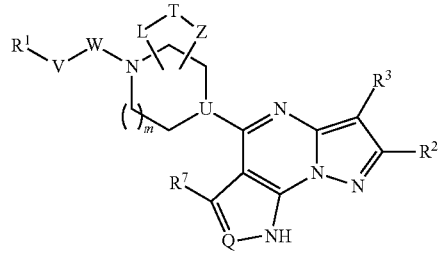

DETAILED DESCRIPTION OF THE INVENTION

The present invention provides Pyrazolopyrrolopyrimidine or dipyrazolopyrimidine Compounds, pharmaceutical compositions comprising a Pyrazolopyrrolopyrimidine or dipyrazolopyrimidine Compound, and methods of using the Pyrazolopyrrolopyrimidine or dipyrazolopyrimidine Compounds for treating cancer in a patient. In addition, the present invention provides methods of using the Pyrazolopyrrolopyrimidine or dipyrazolopyrimidine Compounds for treating a disease or disorder associated with deregulated mTOR activity in a patient.

Compounds

The present invention provides compounds of Formula I

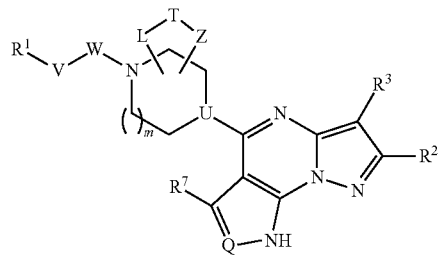

U is N or CH;

W is absent, or W is selected from the group consisting of C(O), S(O), S(O)$_2$, C$_1$-C$_4$ alkylene, C$_3$-C$_8$ cycloalkyl, phenyl, 5- to 6-membered heteroaryl, and 3- to 8-membered heterocyclyl;

V is absent, or V is selected from the group consisting of C(O), O, S, N(H), N(C$_1$-C$_3$ alkyl), N(C$_3$-C$_8$ cycloalkyl), S(O), S(O)$_2$, and C$_1$-C$_4$ alkylene;

or W and V together form a C$_3$-C$_8$ cycloalkyl, phenyl, 5- to 6-membered heteroaryl, or 3 to 8-membered heterocyclyl ring;

R$^1$ is selected from the group consisting of
(i) C$_1$-C$_6$ alkyl or C$_3$-C$_{10}$ cycloalkyl, wherein said alkyl or cycloalkyl of R$^1$ is unsubstituted or substituted with one to three moieties independently selected from the group consisting of hydroxy, C$_1$-C$_6$ alkoxy, halo, trifluoromethyl, carboxy, 5- to 6-membered heteroaryl, —SO$_2$H, C$_1$-C$_6$ alkyl-C(O)—NH—, C$_1$-C$_6$ alkyl-SO$_2$—NH—, and C$_1$-C$_6$ alkyl-SO—NH—;
(ii) 3- to 8-membered heterocyclyl wherein said heterocyclyl of R$^1$ is unsubstituted or substituted with one to three moieties independently selected from the group consisting of halo, C$_1$-C$_6$ alkyl, C$_1$-C$_6$ alkoxy, cyano, hydroxy, amino, C$_1$-C$_6$ alkylamino, and C$_1$-C$_6$ dialkylamino;

(iii) $C_6$-$C_{10}$ aryl or 5- to 10-membered heteroaryl, wherein said aryl or heteroaryl of $R^1$ is unsubstituted or is substituted with one to three moieties independently selected from the group consisting of halo, trifluoromethyl, trifluoromethoxy, $C_1$-$C_6$ alkyl, $C_1$-$C_6$ alkoxy, cyano, hydroxy, amino, $C_1$-$C_6$ alkylamino, and $C_1$-$C_6$ dialkylamino; and (iv) —N(H)OH or —N(H)—$C_1$-$C_3$ alkoxy;

L and Z are bonded to any two carbons of the ring and are independently selected from the group consisting of $CH_2$, $C(H)(R^{10})$, $C(R^{10})(R^{11})$, $N(R^{10})$ C(O), O, S, S(O) and $S(O)_2$;

T is not present such that L is bonded directly to Z, or T is selected from the group consisting of $CH_2$, $C(H)(R^{10})$, $C(R^{10})(R^{11})$, $N(R^{10})$, C(O), O, S, S(O) and $S(O)_2$ and $C_1$-$C_4$ alkylene, wherein said alkylene of T is unsubstituted or substituted with 1 to two substituents selected from the group consisting of $C_1$-$C_3$ alkyl, halo, hydroxyl, $C_1$-$C_3$ alkoxy, amino, $C_1$-$C_3$ alkylamino and $C_1$-$C_3$ dialkylamino;

$R^a$ and $R^b$ are independently selected from H, halogen and $C_1$-$C_6$ alkyl;

$R^2$ is selected from the group consisting of H, halogen, $C_1$-$C_6$alkyl, $C_2$-$C_6$alkenyl, $C_2$-$C_6$alkynyl, $C_1$-$C_6$haloalkyl, $C_3$-$C_8$cycloalkyl, —CN, —$NR^8R^9$, —$OR^9$, —$SR^9$, —$S(O)R^9$, —$S(O_2)R^9$, $C_6$-$C_{10}$aryl, 5- to 10-membered heteroaryl, 5- to 10-membered heterocyclenyl, 5- to 10-membered heterocyclyl, $C_3$-$C_8$cycloalkyl$C_1$-$C_6$alkyl, $C_6$-$C_{10}$aryl$C_1$-$C_6$alkyl, 5- to 10-membered heteroaryl$C_1$-$C_6$alkyl, 5- to 10-membered heterocyclyl$C_1$-$C_6$alkyl, 5- to 10-membered heterocyclenyl$C_1$-$C_6$alkyl;

$R^3$ is selected from the group consisting of H, halogen, $C_1$-$C_6$ alkyl, $C_2$-$C_6$ alkenyl, $C_2$-$C_6$ alkynyl, halo-$C_1$-$C_6$alkyl, —$CF_3$, —$C(O)R^9$, $C_6$-$C_{10}$aryl, $C_3$-$C_8$cycloalkyl, 5- to 10-membered heteroaryl, 5- to 10-membered heterocyclyl, 5- to 10-membered heterocyclenyl, $C_6$-$C_{10}$aryl$C_1$-$C_6$alkyl, $C_3$-$C_8$cycloalkyl$C_1$-$C_6$alkyl, 5- to 10-membered heteroaryl$C_1$-$C_6$alkyl, 5- to 10-membered heterocyclyl$C_1$-$C_6$alkyl and 5- to 10-membered heterocyclenyl$C_1$-$C_6$alkyl, wherein each of said aryl, cycloalkyl, heteroaryl, heterocyclyl, heterocyclenyl, arylalkyl, cycloalkylalkyl, heteroarylalkyl, heterocyclylalkyl and heterocyclenylalkyl is unsubstituted or substituted with one to three moieties which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, —$(CR^aR^b)_nOR^9$, —$(CR^aR^b)_nC(O)R^9$, —$(CR^aR^b)_nNR^8R^9$, —$(CR^aR^b)_nNR^8$, —$NR^8R^9$, —$(CR^aR^b)_nC(O)O$—$C_1$-$C_6$alkyl, —O-halo$C_1$-$C_6$alkyl, —$(CR^aR^b)_nC(O)NR^8R^9$, —$(CR^aR^b)_nC(O)NR^8S(O)_2R^9$, —$(CR^aR^b)_nR^8C(O)R^9$, —$(CR^aR^b)_nNR^8C(O)OR^9$, —$(CR^aR^b)_nR^8C(O)NR^8R^9$, —$(CR^aR^b)_nS(O_2)NR^8R^9$, —$(CR^aR^b)_nS(O_2)NR^8C(O)R^9$, —$(CR^aR^b)_nNR^8S(O_2)R^9$, —$(CR^aR^b)_nSR^9$, —$(CR^aR^b)_nS(O_2)R^9$, $C_6$-$C_{10}$aryl, 5- to 10-membered heteroaryl, 5- to 10-membered heterocyclenyl, 5- to 10-membered heterocyclyl, $C_6$-$C_{10}$arylalkyl, 5- to 10-membered heteroarylalkyl, 5- to 10-membered heterocyclenylalkyl and 5- to 10-membered heterocyclylalkyl wherein each of said alkyl, cycloalkyl, aryl, heteroaryl, heterocyclyl, heterocyclenyl, arylalkyl, cycloalkylalkyl, heteroarylalkyl, heterocyclylalkyl and heterocyclenylalkyl is unsubstituted or substituted with one to five moieties, which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —O-halo$C_1$-$C_6$alkyl, —$OR^9$, —$C(O)R^9$, —$NR^8R^9$, —C(O)O—$C_1$-$C_6$alkyl, —$C(O)NR^8R^9$, —$NR^8C(O)R^9$, —$S(O_2)NR^8R^9$, —$NR^8S(O_2)R^9$, —$SR^9$, and —$S(O_2)R^9$;

$R^6$ and $R^7$ are independently selected from the group consisting of H, halogen, $C_1$-$C_6$alkyl, $C_3$-$C_8$cycloalkyl, —$CF_3$, —CN, —$(CR^aR^b)_nC(O)OH$, —$OCF_3$, —$OR^9$, —$C(O)R^9$, —$NR^8R^9$, —C(O)O—$C_1$-$C_6$alkyl, —$CR^aR^b$, —$OR^a$, —$S(O)R^a$, —$C(O)OR^a$, —$S(O_2)NR^aR^b$, —$NR^aC(O)R^b$, —$NR^aS(O_2)R^b$, —$C(O)NR^8R^9$, —$SR^9$, and —$S(O_2)R^9$;

$R^8$ and $R^9$ are independently selected from the group consisting of H, OH, $C_1$-$C_6$alkyl, $C_3$-$C_8$cycloalkyl, $C_6$-$C_{10}$aryl, 5- to 10-membered heteroaryl, 5- to 10-membered heterocyclenyl, 5- to 10-membered heterocyclyl, $C_3$-$C_8$cycloalkyl$C_1$-$C_6$alkyl, $C_6$-$C_{10}$aryl$C_1$-$C_6$alkyl, 5- to 10-membered heteroaryl$C_1$-$C_6$alkyl, 5- to 10-membered heterocyclyl$C_1$-$C_6$alkyl, 5- to 10-membered heterocyclenyl$C_1$-$C_6$alkyl, and said alkyl, cycloalkyl, aryl, heteroaryl, heterocyclenyl, heterocyclyl, cycloalkylalkyl, arylalkyl, heteroarylalkyl, heterocyclenylalkyl or heterocyclylalkyl is optionally substituted with halogen, $C_1$-$C_6$alkyl, $C_3$-$C_8$cycloalkyl, —$CF_3$, —CN, —$(CR^aR^b)_nC(O)OH$, —$OR^a$, —C(O), amino, —C(O)O—$C_1$-$C_6$alkyl, —$C(O)NR^aR^b$, —$SR^a$, and —$S(O_2)R^a$; or $R^8$ and $R^9$ together with the nitrogen atom to which they are attached form a 3- to 6-membered heterocyclyl ring;

$R^{10}$ and $R^{11}$ are independently selected from the group consisting of H, $C_1$-$C_3$alkyl, halo, hydroxyl, $C_1$-$C_3$alkoxy, amino, $C_1$-$C_3$alkylamino and $C_1$-$C_3$dialkylamino;

Q is N or $CR^6$;

n is independently 0, 1, 2, 3 or 4;

m is independently 0, 1, 2, 3 or 4;

or a pharmaceutically acceptable salt thereof.

In one embodiment of the invention,

L and Z are both $CH_2$, and T is not present;

$R^a$ and $R^b$ are independently selected from H and $C_1$-$C_6$ alkyl;

$R^2$ is H;

$R^3$ is selected from the group consisting of $C_6$-$C_{10}$aryl, 5- to 10-membered heteroaryl, wherein each of said aryl or heteroaryl is unsubstituted or substituted with one to three moieties which can be the same or different, each moiety being selected from the group consisting of halogen, $C_1$-$C_6$alkyl, $C_6$-$C_{10}$aryl, 5- to 10-membered heteroaryl, —$CF_3$, —CN, —C(O)OH, —$(CR^aR^b)_nC(O)OH$, —$OCF_3$, —O-halo$C_1$-$C_6$alkyl, —$OR^8$, —$C(O)R^8$, —$NR^8R^9$, —C(O)O—$C_1$-$C_6$alkyl, —$C(O)NR^8R^9$, —$NR^8C(O)R^9$, —$S(O_2)NR^8R^9$, —$NR^8S(O_2)R^9$, —$SR^8$, and —$S(O_2)R^8$, wherein each of said heteroaryl or aryl is unsubstituted or substituted with one to three moieties, which can be the same or different, each moiety being selected from the group consisting of halogen, $C_1$-$C_6$alkyl, —$CF_3$, —CN, —C(O)OH, —$(CR^aR^b)_nC(O)OH$, —$OCF_3$, —O-halo$C_1$-$C_6$alkyl, —$OR^a$, —$C(O)R^a$, —$NR^aR^b$, —C(O)O—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$;

$R^6$ and $R^7$ are independently selected from the group consisting of H, —$OR^a$, —$NR^aR^b$, —$SR^a$, —$S(O)R^a$, —$S(O_2)R^a$, —$C(O)C_1$-$C_6$alkyl, —$C(O)NR^aR^b$, —$C(O)OR^a$, —$S(O_2)NR^aR^b$, —$NR^aC(O)R^b$, —$NR^aS(O_2)R^b$, $C_1$-$C_6$alkyl, $C_1$-$C_6$alkoxy, halogen, hydroxyl, amino and —CN;

$R^8$ and $R^9$ are independently selected from the group consisting of H, OH, $C_1$-$C_6$alkyl, $C_3$-$C_8$cycloalkyl, $C_6$-$C_{10}$aryl, 5- to 10-membered heteroaryl, 5- to 10-membered heterocyclenyl, 5- to 10-membered heterocyclyl, $C_3$-$C_8$cycloalkyl$C_1$-$C_6$alkyl, $C_6$-$C_{10}$aryl$C_1$-$C_6$alkyl, 5- to 10-membered heteroaryl$C_1$-$C_6$alkyl, 5- to 10-membered heterocyclyl$C_1$-$C_6$alkyl, 5- to 10-membered heterocyclenylC$_1$-C$_6$alkyl, and said alkyl, cycloalkyl, aryl, heteroaryl, heterocyclenyl, heterocyclyl, cycloalkylalkyl, arylalkyl, heteroarylalkyl, heterocyclenylalkyl or heterocyclylalkyl is optionally substituted with halogen, C$_1$-C$_6$alkyl, C$_3$-C$_8$cycloalkyl, —CF$_3$, —CN, —(CR$^a$R$^b$)$_n$C(O)OH, —OCF$_3$, —OR$^a$, —C(O), amino, —C(O)O—C$_1$-C$_6$alkyl, —C(O)NR$^a$R$^b$, —SR$^a$, and —S(O$_2$)R$^a$;

Q is CR$^6$;

n is independently 0, 1 or 2;

m is 1;

or a pharmaceutically acceptable salt thereof.

In another aspect of the foregoing embodiments, W is C(O).

In another aspect of the foregoing embodiments, V is absent.

In yet another aspect of the foregoing embodiments, R$^1$ is selected from the group consisting of:

(i) C$_1$-C$_6$ alkyl or C$_3$-C$_{10}$ cycloalkyl, wherein said alkyl or cycloalkyl of R$^1$ is unsubstituted or substituted with one to three moieties independently selected from the group consisting of hydroxy, C$_1$-C$_6$ alkoxy, fluoro, trifluoromethyl, carboxy, tetrazolyl, —SO$_2$H, C$_1$-C$_6$ alkyl-C(O)—NH—, C$_1$-C$_6$ alkyl-SO$_2$—NH—, and C$_1$-C$_6$ alkyl-SO—NH—; and (ii) 5- to 6-membered heterocyclyl containing 1 to 3 heteroatoms selected from the group consisting of N, O, S, and S(O)$_2$ wherein said heterocyclyl of R$^1$ is unsubstituted or substituted with one to two moieties independently selected from the group consisting of halo, C$_1$-C$_6$ alkyl, C$_1$-C$_6$ alkoxy, cyano, hydroxy, amino, C$_1$-C$_6$ alkylamino, and C$_1$-C$_6$ dialkylamino.

In one embodiment, R$^1$ is selected from the group consisting of:

(i) C$_1$-C$_6$ alkyl, wherein said alkyl of R$^1$ is unsubstituted or substituted with one to three moieties independently selected from the group consisting of hydroxy, C$_1$-C$_6$ alkoxy, fluoro; and (ii) triazol unsubstituted or substituted with one to two moieties independently selected from the group consisting of halo, C$_1$-C$_6$ alkyl, C$_1$-C$_6$ alkoxy, cyano, hydroxy, amino, C$_1$-C$_6$ alkylamino, and C$_1$-C$_6$ dialkylamino.

In another aspect of the foregoing embodiments,

R$^3$ is a 5- to 6-membered heteroaryl or phenyl unsubstituted or substituted with one to three moieties, which can be the same or different, each moiety being selected from the group consisting of halogen, C$_1$-C$_6$alkyl, phenyl, 5- to 6-membered heteroaryl, —CF$_3$, —CN, —C(O)OH, —(CR$^a$R$^b$)$_n$C(O)OH, —O-haloC$_1$-C$_6$alkyl, —C(O)R$^a$, —NR$^a$R$^b$, —C(O)O—C$_1$-C$_6$alkyl, —C(O)NR$^a$R$^b$, —NR$^a$C(O)R$^b$, —S(O$_2$)NR$^a$R$^b$, —NR$^a$S(O$_2$)R$^b$, —SR$^a$, and —S(O$_2$)R$^a$, wherein the alkyl, phenyl or heteroaryl is optionally substituted with one to three moieties, which can be the same or different, each moiety being selected from the group consisting of halogen, C$_1$-C$_6$alkyl, —CF$_3$, —CN, —C(O)OH, —(CR$^a$R$^b$)$_n$C(O)OH, —OCF$_3$, —O—haloC$_1$-C$_6$alkyl, —OR$^a$, —C(O)R$^a$, —NR$^a$R$^b$, —C(O)O—C$_1$-C$_6$alkyl, —C(O)NR$^a$R$^b$, —NR$^a$C(O)R$^b$, —S(O$_2$)NR$^a$R$^b$, —NR$^a$S(O$_2$)R$^b$, —SR$^a$, and —S(O$_2$)R$^a$;

Wherein all other substituents are as defined in any one of claims 1 to 7.

In one embodiment, R$^3$ is pyrazolyl, isoquinolinyl, pyrimidinyl, phenyl or pyridyl, unsubstituted or substituted with one to three moieties, which can be the same or different, each moiety being selected from the group consisting of halogen, C$_1$-C$_6$alkyl, phenyl, 5- to 6-membered heteroaryl, —CF$_3$, —CN, —C(O)OH, —(CR$^a$R$^b$)$_n$C(O)OH, —OCF$_3$, —O-haloC$_1$-C$_6$alkyl, —OR$^a$, —C(O)R$^a$, —NR$^a$R$^b$, —C(O)O—C$_1$-C$_6$alkyl, —C(O)NR$^a$R$^b$, —NR$^a$C(O)R$^b$, —S(O$_2$)NR$^a$R$^b$, —NR$^a$S(O$_2$)R$^b$, —SR$^a$, and —S(O$_2$)R$^a$, wherein the alkyl, phenyl or heteroaryl is optionally substituted with one to three moieties, which can be the same or different, each moiety being selected from the group consisting of halogen, C$_1$-C$_6$alkyl, —CF$_3$, —CN, —C(O)OH, —(CR$^a$R$^b$)$_n$C(O)OH, —OCF$_3$, —O-haloC$_1$-C$_6$alkyl, —OR$^a$, —C(O)R$^a$, —NR$^a$R$^b$, —C(O)O—C$_1$-C$_6$alkyl, —C(O)NR$^a$R$^b$, —NR$^a$C(O)R$^b$, —S(O$_2$)NR$^a$R$^b$, —NR$^a$S(O$_2$)R$^b$, —SR$^a$, and —S(O$_2$)R$^a$.

In another embodiment, R$^3$ is

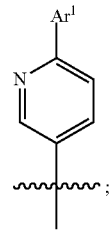

Ar$^1$ is phenyl or a 5- to 6-membered heteroaryl optionally substituted with one to three of R$^{12}$, which can be the same or different, each R$^{12}$ being selected from the group consisting of halogen, C$_1$-C$_6$alkyl, —CF$_3$, —CN, —C(O)OH, —(CR$^a$R$^b$)$_n$C(O)OH, —OCF$_3$, —O-haloC$_1$-C$_6$alkyl, —OR$^a$, —C(O)R$^a$, —NR$^a$R$^b$, —C(O)O—C$_1$-C$_6$alkyl, —C(O)NR$^a$R$^b$, —NR$^a$C(O)R$^b$, —S(O$_2$)NR$^a$R$^b$, —NR$^a$S(O$_2$)R$^b$, —SR$^a$, and —S(O$_2$)R$^a$.

In one embodiment, Ar$^1$ is phenyl, pyridyl, pyrimidinyl, imidazolyl, pyrazinyl, pyrazolyl, or thiazolyl, optionally substituted with one to three of R$^{12}$, which can be the same or different, each R$^{12}$ being selected from the group consisting of halogen, C$_1$-C$_6$alkyl, —CF$_3$, —CN, —C(O)OH, —(CR$^a$R$^b$)$_n$C(O)OH, —OCF$_3$, —O-haloC$_1$-C$_6$alkyl, —OR$^a$, —C(O)R$^a$, —NR$^a$R$^b$, —C(O)O—C$_1$-C$_6$alkyl, —C(O)NR$^a$R$^b$, —NR$^a$C(O)R$^b$, —S(O$_2$)NR$^a$R$^b$, —NR$^a$S(O$_2$)R$^b$, —SR$^a$, and —S(O$_2$)R$^a$.

In another embodiment, R$^{12}$ is selected from the group consisting of halogen, C$_1$-C$_6$alkyl, —CF$_3$, and —OCF$_3$.

In one embodiment, R$^3$ is pyrazolyl, isoquinolinyl, pyrimidinyl, phenyl or pyridyl, unsubstituted or substituted with one to three moieties as defined above.

In one embodiment, R$^3$ is unsubstituted or substituted pyridyl as defined above.

In another embodiment, R$^3$ is

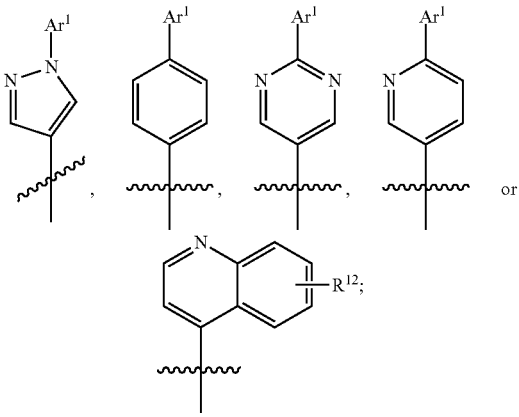

Ar¹ is $C_6$-$C_{10}$aryl or a 5- to 10-membered heteroaryl optionally substituted with one to three of $R^{12}$, which can be the same or different, each $R^{12}$ being selected from the group consisting of halogen, $C_1$-$C_6$alkyl, —$CF_3$, —CN, —C(O)OH, —$(CR^aR^b)_nC(O)OH$, —$OCF_3$, —O-halo$C_1$-$C_6$alkyl, —$OR^a$, —$C(O)R^a$, —$NR^aR^b$, —$C(O)O$—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$. In one embodiment, Ar¹ is phenyl or a 5- to 6-membered heteroaryl optionally substituted.

In a another embodiment, $R^3$ is

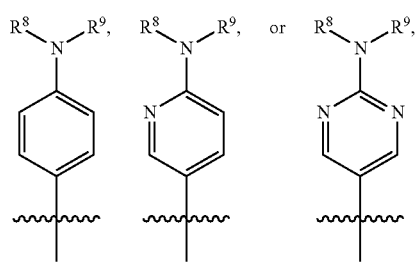

wherein $R^8$ and $R^9$ are as defined above. In one embodiment, $R^8$ is H and $R^9$ is cyclopropyl.

In a further embodiment, Ar¹ is phenyl, pyrazolyl, pyrimidinyl, pyridyl, imidazolyl, pyrazinyl or thiazolyl optionally substituted with one to three of $R^{12}$. In a another embodiment, Ar¹ is phenyl, pyridyl or imidazolyl optionally substituted with one to three of $R^{12}$.

In another embodiment, $R^3$ is

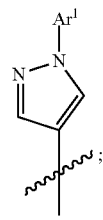

Ar¹ is phenyl, pyridyl, pyrazinyl or imidazolyl optionally substituted with one to three of $R^{12}$ as defined above.

In another embodiment, $R^3$ is

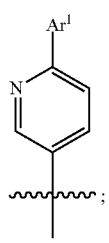

Ar¹ is phenyl, pyridyl, pyrazinyl or imidazolyl optionally substituted with one to three of $R^{12}$ as defined above.

In another embodiment, $R^3$ is selected from the group consisting of

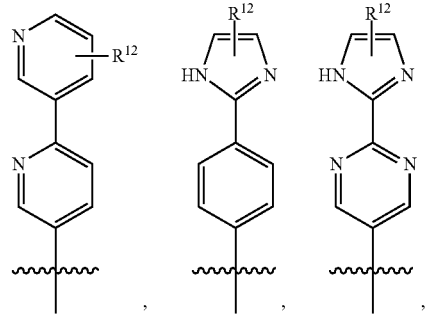

,

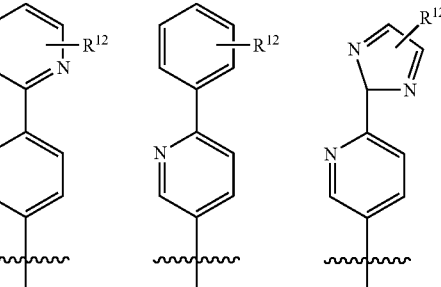

,

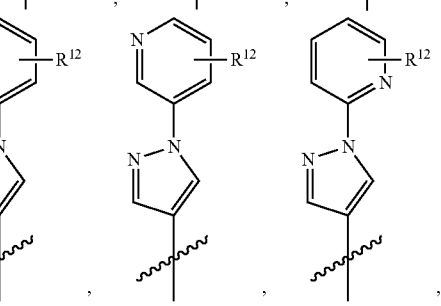

, and

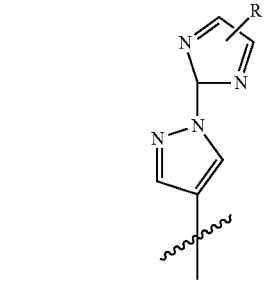

, and $R^{12}$ is defined above.

In one embodiment, in the foregoing embodiments, $R^{12}$ is selected from the group consisting of halogen, $C_1$-$C_6$alkyl, —$CF_3$, and —$OCF_3$. In another embodiment, $R^{12}$ is selected from the group consisting of F and methyl.

In one embodiment, $R^6$ and $R^7$ are independently selected from the group consisting of H, halo, —$C(O)C_1$-$C_6$alkyl, —$S(O)_2C_1$-$C_6$alkyl and CN; and all other substituents are as defined above. In another aspect of the foregoing embodiments, $R^6$ is H or $C_1$-$C_6$alkyl and $R^7$ is H or $C_1$-$C_6$alkyl. In another aspect of the foregoing embodiments, $R^6$ is H and $R^7$ is H.

Specific embodiments depicting non-limiting Examples of the above Formulas are provided in the Experimental Section hereinbelow.

Specific examples of the compounds of the instant invention include:

((1R,3s,5S)-3-(3-methyl-6-(6-phenylpyridin-3-yl)-1H-dipyrazolo[1,5-a:4',3'-e]pyrimidin-4-yl)-8-azabicyclo[3.2.1]octan-8-yl)(4H-1,2,4-triazol-3-yl)methanone;

((1R,3s,5S)-3-(3-(6-phenylpyridin-3-yl)-8H-pyrazolo[1,5-a]pyrrolo[3,2-e]pyrimidin-5-yl)-8-azabicyclo[3.2.1]octan-8-yl)(4H-1,2,4-triazol-3-yl)methanone;

((1R,3s,5S)-3-(3-(6-(2-hydroxypropan-2-yl)pyridin-3-yl)-8H-pyrazolo[1,5-a]pyrrolo[3,2-e]pyrimidin-5-yl)-8-azabicyclo[3.2.1]octan-8-yl)(1H-1,2,4-triazol-3-yl)methanone;

2-hydroxy-1-((1R,3s,5S)-3-(3-(6-(2-hydroxypropan-2-yl)pyridin-3-yl)-8H-pyrazolo[1,5-a]pyrrolo[3,2-e]pyrimidin-5-yl)-8-azabicyclo[3.2.1]octan-8-yl)ethanone;

1-((1R,3s,5S)-3-(3-(6-(1H-imidazol-2-yl)pyridin-3-yl)-8H-pyrazolo[1,5-a]pyrrolo[3,2-e]pyrimidin-5-yl)-8-azabicyclo[3.2.1]octan-8-yl)-2-hydroxyethanone; and ((1R,3s,5S)-3-(3-(6-(1H-imidazol-2-yl)pyridin-3-yl)-8H-pyrazolo[1,5-a]pyrrolo[3,2-e]pyrimidin-5-yl)-8-azabicyclo[3.2.1]octan-8-yl)(4H-1,2,4-triazol-3-yl)methanone;

Or a stereoisomer thereof;

Or a pharmaceutically acceptable salt thereof;

Or a pharmaceutically acceptable salt of the stereoisomer thereof

Chemical Definitions

As used herein, "alkyl" is intended to include both branched and straight-chain saturated aliphatic hydrocarbon groups having the specified number of carbon atoms. For example, $C_1$-$C_{10}$, as in "$C_1$-$C_{10}$alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, i-butyl, pentyl, hexyl, heptyl, octyl, nonyl, decyl, and so on.

When used in the phrases "alkylaryl", "alkylcycloalkyl" and "alkylheterocyclyl" the term "alkyl" refers to the alkyl portion of the moiety and does not describe the number of atoms in the heterocyclyl portion of the moiety. In an embodiment, if the number of carbon atoms is not specified, the "alkyl" of "alkylaryl", "alkylcycloalkyl" and "alkylheterocyclyl" refers to $C_1$-$C_{12}$ alkyl and in a further embodiment, refers to $C_1$-$C_6$ alkyl.

The term "cycloalkyl" means a monocyclic saturated or unsaturated aliphatic hydrocarbon group having the specified number of carbon atoms. The cycloalkyl is optionally bridged (i.e., forming a bicyclic moiety), for example with a methylene, ethylene or propylene bridge. The cycloalkyl may be fused with an aryl group such as phenyl, and it is understood that the cycloalkyl substituent is attached via the cycloalkyl group. For example, "cycloalkyl" includes cyclopropyl, methyl-cyclopropyl, 2,2-dimethyl-cyclobutyl, 2-ethyl -cyclopentyl, cyclohexyl, cyclopentenyl, cyclobutenyl and so on.

In an embodiment, if the number of carbon atoms is not specified, "alkyl" refers to $C_1$-$C_{12}$ alkyl and in a further embodiment, "alkyl" refers to $C_1$-$C_6$ alkyl. In an embodiment, if the number of carbon atoms is not specified, "cycloalkyl" refers to $C_3$-$C_{10}$ cycloalkyl and in a further embodiment, "cycloalkyl" refers to $C_3$-$C_7$ cycloalkyl. In an embodiment, examples of "alkyl" include methyl, ethyl, n-propyl, i-propyl, n-butyl, t-butyl and i-butyl.

The term "alkylene" means a hydrocarbon diradical group having the specified number of carbon atoms. For example, "alkylene" includes —$CH_2$—, —$CH_2CH_2$— and the like. In an embodiment, if the number of carbon atoms is not specified, "alkylene" refers to $C_1$-$C_{12}$ alkylene and in a further embodiment, "alkylene" refers to $C_1$-$C_6$ alkylene.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl, 2-methylbutenyl and cyclohexenyl. The straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "$C_2$-$C_6$ alkynyl" means an alkynyl radical having from 2 to 6 carbon atoms. Alkynyl groups include ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

"Aryl" is intended to mean any stable monocyclic, bicyclic or tricyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

In one embodiment, "aryl" is an aromatic ring of 6 to 14 carbons atoms, and includes a carbocyclic aromatic group fused with a 5- or 6-membered cycloalkyl group such as indan. Examples of carbocyclic aromatic groups include, but are not limited to, phenyl, naphthyl, e.g. 1-naphthyl and 2-naphthyl; anthracenyl, e.g. 1-anthracenyl, 2-anthracenyl; phenanthrenyl; fluorenonyl, e.g. 9-fluorenonyl, indanyl and the like.

The term heteroaryl, as used herein, represents a stable monocyclic, bicyclic or tricyclic ring of up to 7 atoms in each ring, wherein at least one ring is aromatic and contains carbon and from 1 to 4 heteroatoms selected from the group consisting of O, N and S. In another embodiment, the term heteroaryl refers to a monocyclic, bicyclic or tricyclic aromatic ring of 5- to 14-ring atoms of carbon and from one to four heteroatoms selected from O, N, or S. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

Heteroaryl groups within the scope of this definition include but are not limited to acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. Additional examples of heteroaryl include, but are not limited to pyridyl, e.g., 2-pyridyl (also referred to as α-pyridyl), 3-pyridyl (also referred to as β-pyridyl) and 4-pyridyl (also referred to as (γ-pyridyl); thienyl, e.g., 2-thienyl and 3-thienyl; furanyl, e.g., 2-furanyl and 3-furanyl; pyrimidyl, e.g., 2-pyrimidyl and 4-pyrimidyl; imidazolyl, e.g., 2-imidazolyl; pyranyl, e.g., 2-pyranyl and 3-pyranyl; pyrazolyl, e.g., 4-pyrazolyl and 5-pyrazolyl; thiazolyl, e.g., 2-thiazolyl, 4-thiazolyl and 5-thiazolyl; thiadiazolyl; isothiazolyl; oxazolyl, e.g., 2-oxazoyl, 4-oxazoyl and 5-oxazoyl; isoxazoyl; pyrrolyl; pyridazinyl; pyrazinyl and the like.

In an embodiment, "heteroaryl" may also include a "fused polycyclic aromatic", which is a heteroaryl fused with one or more other heteroaryl or nonaromatic heterocyclic ring. Examples include, quinolinyl and isoquinolinyl, e.g. 2-quinolinyl, 3-quinolinyl, 4-quinolinyl, 5-quinolinyl, 6-quinolinyl, 7-quinolinyl and 8-quinolinyl, 1-isoquinolinyl, 3-quinolinyl, 4-isoquinolinyl, 5-isoquinolinyl, 6-isoquinolinyl, 7-isoquinolinyl and 8-isoquinolinyl; benzofuranyl, e.g. 2-benzofuranyl and 3-benzofuranyl; dibenzofuranyl, e.g. 2,3-dihydrobenzofuranyl; dibenzothiophenyl; benzothienyl, e.g. 2-benzothienyl and 3-benzothienyl; indolyl, e.g. 2-indolyl and 3-indolyl; benzothiazolyl, e.g., 2-benzothiazolyl; benzooxazolyl, e.g., 2-benzooxazolyl; benzimidazolyl, e.g. 2-benzoimidazolyl; isoindolyl, e.g. 1-isoindolyl and 3-isoindolyl; benzotriazolyl; purinyl; thianaphthenyl, pyrazinyl and the like.

"Heterocyclyl" means a non-aromatic saturated monocyclic, bicyclic, tricyclic or spirocyclic ring system comprising up to 7 atoms in each ring. Preferably, the heterocyclyl contains 3 to 14, or 5 to 10 ring atoms, in which one or more of the atoms in the ring system is an element other than carbon, for example, nitrogen, oxygen, phosphor or sulfur, alone or in combination. There are no adjacent oxygen and/or sulfur atoms present in the ring system. Preferred heterocyclyls contain about 5 to about 6 ring atoms. The heterocycle may be fused with an aromatic aryl group such as phenyl or heterocyclenyl. The prefix aza, oxa or thia before the heterocyclyl root name means that at least a nitrogen, oxygen or sulfur atom, respectively, is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes heterocyclyl rings as described above wherein =O replaces two available hydrogens on the same ring carbon atom. An example of such a moiety is pyrrolidone:

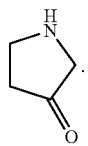

In describing the heteroatoms contained in a specified heterocyclyl group, the expression, "having one to x heteroatoms selected from the group of N, O, P and S" (wherein x is an a specified integer), for example, means that each heteroatom in the specified heterocyclyl is independently selected from the specified selection of heteroatoms. Attachment of a heterocyclyl substituent can occur via a carbon atom or via a heteroatom.

"Heterocyclenyl" means a non-aromatic monocyclic, bicyclic, tricyclic or spirocyclic ring system comprising up to 7 atoms in each ring. Preferably, the heterocyclenyl contains 3 to 14, or 5 to 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen, phosphor or sulfur atom respectively is present as a ring atom. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes heterocyclenyl rings as described above wherein =O replaces two available hydrogens on the same ring carbon atom. An example of such a moiety is pyrrolidinone:

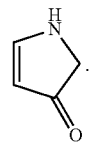

In describing the heteroatoms contained in a specified heterocyclenyl group, the expression, "having one to x heteroatoms selected from the group of N, O, P and S" (wherein x is an a specified integer), for example, means that each heteroatom in the specified heterocyclenyl is independently selected from the specified selection of heteroatoms.

It should also be noted that tautomeric forms such as, for example, the moieties:

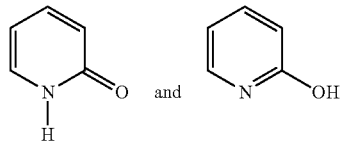 [SMILES: O=c1cccc[nH]1 ; Oc1ccccn1]

are considered equivalent in certain embodiments of this invention.

An "alkylaryl group" is an alkyl group substituted with an aryl group, for example, a phenyl group. Suitable aryl groups are described herein and suitable alkyl groups are described herein. The bond to the parent moiety is through the aryl group.

An "alkylheteroaryl group" is an alkyl group substituted with a heteroaryl group. Suitable heteroaryl groups are described herein and suitable alkyl groups are described herein. The bond to the parent moiety is through the heteroaryl group.

An "alkylheterocyclyl group" is an alkyl group substituted with a heterocyclyl group. Suitable heterocyclyl groups are described herein and suitable alkyl groups are described herein. The bond to the parent moiety is through the heterocyclyl group.

An "alkylheterocyclenyl group" is an alkyl group substituted with a heterocyclenyl group. Suitable heterocyclenyl groups are described herein and suitable alkyl groups are described herein. The bond to the parent moiety is through the heterocyclenyl group.

An "alkylcycloalkyl group" is an alkyl group substituted with a cycloalkyl group. Suitable cycloalkyl groups are described herein and suitable alkyl groups are described herein. The bond to the parent moiety is through the cycloalkyl group.

An "arylalkyl group" is an aryl group substituted with an alkyl group, for example, a phenyl group. Suitable aryl groups are described herein and suitable alkyl groups are described herein. The bond to the parent moiety is through the alkyl group.

A "heteroarylalkyl group" is a heteroaryl group substituted with an alkyl group. Suitable heteroaryl groups are described herein and suitable alkyl groups are described herein. The bond to the parent moiety is through the alkyl group.

A "heterocyclylalkyl group" is a heterocyclyl group substituted with an alkyl group. Suitable heterocyclyl groups are described herein and suitable alkyl groups are described herein. The bond to the parent moiety is through the alkyl group.

A "heterocyclenylalkyl group" is a heterocyclenyl group substituted with an alkyl group. Suitable heterocyclenyl groups are described herein and suitable alkyl groups are described herein. The bond to the parent moiety is through the alkyl group.

A "cycloalkylalkyl group" is a cycloalkyl group substituted with an alkyl group. Suitable cycloalkyl groups are described herein and suitable alkyl groups are described herein. The bond to the parent moiety is through the alkyl group.

An "aryloxy group" is an aryl group that is attached to a compound via an oxygen (e.g., phenoxy).

An "alkoxy group" (alkyloxy), as used herein, is a straight chain or branched $C_1$-$C_{12}$ or cyclic $C_3$-$C_{12}$ alkyl group that is connected to a compound via an oxygen atom. Examples of alkoxy groups include but are not limited to methoxy, ethoxy and propoxy.

An "arylalkoxy group" (arylalkyloxy) is an arylalkyl group that is attached to a compound via an oxygen on the alkyl portion of the arylalkyl (e.g., phenylmethoxy).

An "arylamino group" as used herein, is an aryl group that is attached to a compound via a nitrogen.

An "alkylamino group" as used herein, is an alkyl group that is attached to a compound via a nitrogen.

As used herein, an "arylalkylamino group" is an arylalkyl group that is attached to a compound via a nitrogen on the alkyl portion of the arylalkyl.

An "alkylsulfonyl group" as used herein, is an alkyl group that is attached to a compound via the sulfur of a sulfonyl group.

When a moiety is referred to as "unsubstituted" or not referred to as "substituted" or "optionally substituted", it means that the moiety does not have any substituents. When a moiety is referred to as substituted, it denotes that any portion of the moiety that is known to one skilled in the art as being available for substitution can be substituted. The phrase "optionally substituted with one or more substituents" means, in one embodiment, one substituent, two substituents, three substituents, four substituents or five substituents. For example, the substitutable group can be a hydrogen atom that is replaced with a group other than hydrogen (i.e., a substituent group). Multiple substituent groups can be present. When multiple substituents are present, the substituents can be the same or different and substitution can be at any of the substitutable sites. Such means for substitution are well known in the art. For purposes of exemplification, which should not be construed as limiting the scope of this invention, some examples of groups that are substituents are: alkyl, alkenyl or alkynyl groups (which can also be substituted, with one or more substituents), alkoxy groups (which can be substituted), a halogen or halo group (F, Cl, Br, I), hydroxy, nitro, oxo, —CN, —COH, —COOH, amino, azido, N-alkylamino or N,N-dialkylamino (in which the alkyl groups can also be substituted), N-arylamino or N,N-diarylamino (in which the aryl groups can also be substituted), esters (—C(O)—OR, where R can be a group such as alkyl, aryl, etc., which can be substituted), ureas (—NHC(O)—NHR, where R can be a group such as alkyl, aryl, etc., which can be substituted), carbamates (—NHC(O)—OR, where R can be a group such as alkyl, aryl, etc., which can be substituted), sulfonamides (—NHS(O)$_2$R, where R can be a group such as alkyl, aryl, etc., which can be substituted), alkylsulfonyl (which can be substituted), aryl (which can be substituted), cycloalkyl (which can be substituted)alkylaryl (which can be substituted), alkylheterocyclyl (which can be substituted), alkylcycloalkyl (which can be substituted), and aryloxy.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Certain isotopically-labelled compounds of Formula (I) can be useful for medical imaging purposes. For instance those compounds labeled with positron-emitting isotopes like $^{11}$C or $^{18}$F can be useful for application in Positron Emission Tomography (PET) and those labeled with gamma ray emitting isotopes like $^{123}$I can be useful for application in Single Photon Emission Computed Tomography (SPECT). Additionally, isotopic substitution of a compound at a site where epimerization occurs may slow or reduce the epimerization process and thereby retain the more active or efficacious form of the compound for a longer period of time.

It is also possible that the compounds of Formula (I) may exist in different tautomeric forms, and all such forms are embraced within the scope of the invention. Also, for example, all keto-enol and imine-enamine forms of the compounds are included in the invention.

Stereochemistry

When structures of the same constitution differ in respect to the spatial arrangement of certain atoms or groups, they are stereoisomers, and the considerations that are significant in analyzing their interrelationships are topological. If the relationship between two stereoisomers is that of an object and its nonsuperimposable minor image, the two structures are enantiomeric, and each structure is said to be chiral. Stereoisomers also include diastereomers, cis-trans isomers and conformational isomers. Diastereoisomers can be chiral or achiral, and are not mirror images of one another. Cis-trans isomers differ only in the positions of atoms relative to a specified planes in cases where these atoms are, or are considered as if they were, parts of a rigid structure. Conformational isomers are isomers that can be interconverted by rotations about formally single bonds. Examples of such conformational isomers include cyclohexane conformations with chair and boat conformers, carbohydrates, linear alkane conformations with staggered, eclipsed and gauche confomers, etc. See J. Org. Chem. 35, 2849 (1970)

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, enantiomers are identical except that they are non-superimposable mirror images of one another. A mixture of enantiomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the Formulas of the invention, it is understood that both the (R) and (S) configurations of the chiral carbon, and hence both enantiomers and mixtures thereof, are embraced within the Formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

When the compounds of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Designation of a specific absolute configuration at a chiral carbon of the compounds of the invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50%. In a particular embodiment when a specific absolute configuration is designated, the enantiomeric excess of depicted compounds is at least about 90%.

When a compound of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated as described above. The present invention includes each diastereoisomer of such compounds and mixtures thereof.

As used herein, "a," "an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

This invention is also intended to encompass pro-drugs of the pyrazolopyrrolopyrimidine or dipyrazolopyrimidine compounds disclosed herein. A prodrug of any of the compounds can be made using well-known pharmacological techniques.

Pharmaceutically Acceptable Salts

The pyrazolopyrrolopyrimidine or dipyrazolopyrimidine compounds described herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts organic and inorganic acids, for example, acid addition salts which may, for example, be hydrochloric acid, sulphuric acid, methanesulphonic acid, fumaric acid, maleic acid, succinic acid, acetic acid, benzoic acid, oxalic acid, citric acid, tartaric acid, carbonic acid, phosphoric acid, trifluoroacetic acid, formic acid and the like. Pharmaceutically acceptable salts can also be prepared from by treatment with inorganic bases, for example, sodium, potassium, ammonium, calcium, or ferric hydroxides, and such organic bases as isopropylamine, trimethylamine, 2-ethylamino ethanol, histidine, procaine, and the like. Pharmaceutically acceptable salts can also be formed from elemental anions such as chlorine, bromine and iodine.

The active compounds disclosed can, as noted above, also be prepared in the form of their hydrates. The term "hydrate" includes but is not limited to hemihydrate, monohydrate, dihydrate, trihydrate, tetrahydrate and the like.

The active compounds disclosed can, as noted above, also be prepared in the form of a solvate with any organic or inorganic solvent, for example alcohols such as methanol, ethanol, propanol and isopropanol, ketones such as acetone, aromatic solvents and the like.

The active compounds disclosed can also be prepared in any solid or liquid physical form. For example, the compound can be in a crystalline form, in amorphous form, and have any particle size. Furthermore, the compound particles may be micronized, or may be agglomerated, particulate granules, powders, oils, oily suspensions or any other form of solid or liquid physical form.

The compounds of the present invention may also exhibit polymorphism. This invention further includes different polymorphs of the compounds of the present invention. The term "polymorph" refers to a particular crystalline state of a substance, having particular physical properties such as X-ray diffraction, IR spectra, melting point, and the like.

As used herein, "a," an" and "the" include singular and plural referents unless the context clearly dictates otherwise. Thus, for example, reference to "an active agent" or "a pharmacologically active agent" includes a single active agent as well a two or more different active agents in combination, reference to "a carrier" includes mixtures of two or more carriers as well as a single carrier, and the like.

Methods of Treatment

The Pyrazolopyrrolopyrimidine or dipyrazolopyrimidine Compounds may be useful in human and veterinary medicine in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974, which is hereby incorporated by reference.

While not being bound by any specific theory it is believed that the Pyrazolopyrrolopyrimidine or dipyrazolopyrimidine Compounds may be useful in the treatment of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease because of their mTOR inhibitory activity.

The general value of the compounds of the invention in inhibiting mTOR can be determined, for example, using the assay described in Example 7. In addition, the general value in inhibiting mTORC1 or mTORC2 function can be evaluated using the assays described in Example 8.

More specifically, the Pyrazolopyrrolopyrimidine or dipyrazolopyrimidine Compounds can be useful in the treatment of a variety of cancers, including (but not limited to) the following:

tumor of the bladder, breast (including BRCA-mutated breast cancer), colorectal, colon, kidney, liver, lung, small cell lung cancer, non-small cell lung cancer, head and neck, esophagus, bladder, gall bladder, ovary, pancreas, stomach, cervix, thyroid, prostate, and skin, including squamous cell carcinoma;

leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma and Burkett's lymphoma;

chronic lymphocytic leukemia ("CLL"), acute and chronic myelogenous leukemia, myelodysplastic syndrome and promyelocytic leukemia;

fibrosarcoma, rhabdomyosarcoma;

head and neck, mantle cell lymphoma, myeloma;

astrocytoma, neuroblastoma, glioma, glioblastoma, malignant glial tumors, astrocytoma, hepatocellular carcinoma, gastrointestinal stromal tumors ("GIST") and schwannomas;

melanoma, multiple myeloma, seminoma, teratocarcinoma, osteosarcoma, xenoderma pigmentosum, keratoctanthoma, thyroid follicular cancer, endometrial cancer, gastrointestinal tract cancer and Kaposi's sarcoma.

While not being bound by any specific theory, due to the key role of kinases in the regulation of cellular proliferation in general, inhibitors of kinases could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The Pyrazolopyrrolopyrimidine or dipyrazolopyrimidine Compounds may induce or inhibit apoptosis. The apoptotic response is aberrant in a variety of human diseases. The Pyrazolopyrrolopyrimidine or dipyrazolopyrimidine Compounds, as modulators of apoptosis, can be useful in the treatment of cancer (including but not limited to those types mentioned hereinabove), viral infections (including, but not limited to, herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

While not being bound by any specific theory, the Pyrazolopyrrolopyrimidine or dipyrazolopyrimidine Compounds, as inhibitors of kinases, can modulate the level of cellular RNA and DNA synthesis. These compounds would therefore be useful in the treatment of viral infections (including but not limited to HIV, human papilloma virus, herpesvirus, poxvirus, Epstein-Barr virus, Sindbis virus and adenovirus).

In particular embodiments of the invention, Pyrazolopyrrolopyrimidine or dipyrazolopyrimidine Compounds, as inhibitors of mTOR kinase could act in diseases or disorders other than cancer that are associated with dysregulated mTOR activity such as viral infections (including, but not limited to, herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The Pyrazolopyrrolopyrimidine or dipyrazolopyrimidine Compounds may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

The Pyrazolopyrrolopyrimidine or dipyrazolopyrimidine Compounds may also be useful in inhibiting tumor angiogenesis and metastasis.

Another aspect of this invention is a method of treating a patient (e.g., human) having a disease or condition associated with mTOR kinases by administering a therapeutically effective amount of a Pyrazolopyrrolopyrimidine or dipyrazolopyrimidine Compound, or a pharmaceutically acceptable salt of said compound to the patient.

The present invention provides a method of treating cancer comprising the step of administering to a subject a therapeutically effective amount of the Pyrazolopyrrolopyrimidine or dipyrazolopyrimidine Compounds. The present invention also provides the Use of the Pyrazolopyrrolopyrimidine or dipyrazolopyrimidine Compounds for the preparation of a medicament for the treatment of cancer. The invention also provides the Pyrazolopyrrolopyrimidine or dipyrazolopyrimidine Compounds for use in the treatment of cancer.

In the therapies described above, an example dosage for administration to a patient is about 0.001 to 1000 mg/kg of body weight/day of the Pyrazolopyrrolopyrimidine or dipyrazolopyrimidine Compound. Another example dosage is about 0.01 to 25 mg/kg of body weight/day of the Pyrazolopyrrolopyrimidine or dipyrazolopyrimidine Compound, or a pharmaceutically acceptable salt of said compound.

The dosage regimen utilizing the compounds of the present invention can be selected in accordance with a variety of factors including type, species, age, weight, sex and the type of cancer being treated; the severity (i.e., stage) of the disease to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

Definitions

As used herein, the term "therapeutically effective amount" means that amount of active compound or pharmaceutical agent that elicits the biological or medicinal response in a tissue, system, animal or human that is being sought by a researcher, veterinarian, medical doctor or other clinician. The therapeutic effect is dependent upon the disease or disorder being treated or the biological effect desired. As such, the therapeutic effect can be a decrease in the severity of symptoms associated with the disease or disorder and/or inhibition (partial or complete) of progression of the disease. The amount needed to elicit the therapeutic response can be determined based on the age, health, size and sex of the subject. Optimal amounts can also be determined based on monitoring of the subject's response to treatment.

Further, a therapeutically effective amount, can be an amount that selectively induces terminal differentiation, cell growth arrest and/or apoptosis of neoplastic cells, or an amount that induces terminal differentiation of tumor cells.

The method of the present invention is intended for the treatment or chemoprevention of human patients with cancer. However, it is also likely that the method would be effective in the treatment of cancer in other subjects. "Subject", as used herein, refers to animals such as mammals, including, but not limited to, primates (e.g., humans), cows, sheep, goats, horses, pigs, dogs, cats, rabbits, guinea pigs, rats, mice or other bovine, ovine, equine, canine, feline, rodent or murine species.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

Combination Therapy

The compounds of the present invention can be administered alone or in combination with other therapies suitable for the disease or disorder being treated. Where separate dosage formulations are used, the compound and the other therapeutic agent can be administered at essentially the same time (concurrently) or at separately staggered times (sequentially). The pharmaceutical combination is understood to include all these regimens. Administration in these various ways are suitable for the present invention as long as the beneficial therapeutic effect of the compound and the other therapeutic agent are realized by the patient at substantially the same time. In an embodiment, such beneficial effect is achieved when the target blood level concentrations of each active drug are maintained at substantially the same time.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Therefore, the present invention encompasses pharmaceutical compositions comprising a therapeutically effective amount of the compound of the invention and a pharmaceutically acceptable carrier and optionally other threrapeutic ingredients, such as an anti-cancer agent. Examples of such agents can be found in *Cancer Principles and Practice of Oncology* by V.T. Devita and S. Hellman (editors), 6th edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents, agents that interfere with cell cycle checkpoints, agents that interfere with receptor tyrosine kinases (RTKs) and cancer vaccines. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, diethylstibestral, tamoxifen, raloxifene, idoxifene, LY353381, LY117081, toremifene, fluoxymestero, lfulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

Other hormonal agents include: aromatase inhibitors (e.g., aminoglutethimide, anastrozole and tetrazole), luteinizing hormone release hormone (LHRH) analogues, ketoconazole, goserelin acetate, leuprolide, megestrol acetate and mifepristone.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, chlorambucil, cyclophosphamide, ifosfamide, mechlorethamine, melphalan, uracil mustard, thiotepa, busulfan, carmustine, lomustine, streptozocin, tasonermin, lonidamine, carboplatin, altretamine, dacarbazine, procarbazine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl -pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, doxorubicin, daunorubicin, idarubicin, anthracenedione, bleomycin, mitomycin C, dactinomycin, plicatomycin, bisantrene, mitoxantrone, pirarubicin, pinafide, valrubicin, amrubicin, antineoplaston, 3'-deamino -3'-morpholino-13-deoxo-10-hydroxycarminomycin, annamycin, galarubicin, elinafide, MEN10755, and 4-demethoxy-3-deamino-3-aziridinyl-4-methylsulphonyl -daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include vincristine, vinblastine, vindesine, vinzolidine, vinorelbine, vindesine sulfate, 3',4'-didehydro-4'-deoxy-8'-norvincaleukoblastine, podophyllotoxins (e.g., etoposide (VP-16) and teniposide (VM-26)), paclitaxel, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroOxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678, WO 03/39460 and WO2003/079973, WO2003/099211, WO2004/039774, WO2003/105855, WO2003/106417. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamflatin, PXD101, MG98, valproic acid and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, floxuridine, methotrexate, leucovarin, hydroxyurea, thioguanine (6-TG), mercaptopurine (6-MP), cytarabine, pentostatin, fludarabine phosphate, cladribine (2-CDA), asparaginase, gemcitabine, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D -arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589, 485, and 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, erythropoietin (epoietin-α), granulocyte-CSF (filgrastin), granulocyte, macrophage-CSF (sargramostim), pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); JNCI, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop*. Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl) -fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs shown as described by Bume-Jensen and Hunter, Nature, 411:355-365, 2001.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of CD20 (rituximab), inhibitors of cytokine receptors, inhibitors of MET, inhibitors of PI3K family kinase (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY-43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

Examples of mTOR inhibitors include ridaforolimus, temsirolimus, everolimus, a rapamycin-analog. Ridaforolimus, also known as AP 23573, MK-8669 and deforolimus, is a unique, non-prodrug analog of rapmycin that has antiproliferative activity in a broad range of human tumor cell lines in vitro and in murine tumor xenograft models utilizing human tumor cell lines. Ridaforolimus has been administered to patients with advanced cancer and is currently in clinical development for various advanced malignancies, including studies in patients with advanced soft tissue or bone sarcomas. Thus far, these trials have demonstrated that ridaforolimus is generally well-tolerated with a predictable and manageable adverse even profile, and possess anti-tumor activity in a broad range of cancers. A description and preparation of ridaforolimus is described in U.S. Pat. No. 7,091,213 to Ariad Gene Therapeutics, Inc.

Temsirolimus, also known as Torisel®, is currently marketed for the treatment of renal cell carcinoma. A description and preparation of temsirolimus is described in U.S. Pat. No. 5,362,718 to American Home Products Corporation. Everolimus, also known as Certican® or RAD001, marketed by Novartis, has greater stability and enhanced solubility in organic solvents, as well as more favorable pharmokinetics with fewer side effects than rapamycin (sirolimus). Everolimus has been used in conjunction with microemulsion cyclosporin (Neoral®, Novartis) to increase the efficacy of the immunosuppressive regime.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, and 5,710,140, WO 94/15932, U.S. Pat. Nos. 5,344,991, 5,134, 142, 5,380,738, 5,393,790, 5,466,823, 5,633,272, and 5,932, 598.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H -diindolo[1,2,3-fg:3',2',1'-kl]pyrrolo [3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD 121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.*

2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet* 61:785-789, 1997) and Kufe et al (*Cancer Medicine*, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), Duc-4, NF-1, NF-2, RB, WT1, BRCA1, BRCA2, a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, bacillus Calmette-Guerin, octreotide, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to anastrozole, letrozole and exemestane.

A compound of the instant invention may also be useful for treating or preventing cancer in combination with siRNA therapeutics.

A compound of the instant invention may also be useful for treating or preventing cancer in combination with compounds which induce terminal differentiation of the neoplastic cells. Suitable differentiation agents include the compounds disclosed in any one or more of the following references.

a) Polar compounds (Marks et al (1987); Friend, C., Scher, W., Holland, J. W., and Sato, T. (1971) *Proc. Natl. Acad. Sci.* (USA) 68: 378-382; Tanaka, M., Levy, J., Terada, M., Breslow, R., Rifkind, R. A., and Marks, P. A. (1975) *Proc. Natl. Acad. Sci.* (USA) 72: 1003-1006; Reuben, R. C., Wife, R. L., Breslow, R., Rifkind, R. A., and Marks, P. A. (1976) *Proc. Natl. Acad. Sci.* (USA) 73: 862-866);

b) Derivatives of vitamin D and retinoic acid (Abe, E., Miyaura, C., Sakagami, H., Takeda, M., Konno, K., Yamazaki, T., Yoshika, S., and Suda, T. (1981) *Proc. Natl. Acad. Sci.* (USA) 78: 4990-4994; Schwartz, E. L., Snoddy, J. R., Kreutter, D., Rasmussen, H., and Sartorelli, A. C. (1983) *Proc. Am. Assoc. Cancer Res.* 24: 18; Tanenaga, K., Hozumi, M., and Sakagami, Y. (1980) *Cancer Res.* 40: 914-919);

c) Steroid hormones (Lotem, J. and Sachs, L. (1975) *Int. J. Cancer* 15: 731-740);

d) Growth factors (Sachs, L. (1978) *Nature (Lond.)* 274: 535, Metcalf, D. (1985) *Science,* 229: 16-22);

e) Proteases (Scher, W., Scher, B. M., and Waxman, S. (1983) *Exp. Hematol.* 11: 490-498; Scher, W., Scher, B. M., and Waxman, S. (1982) *Biochem. & Biophys. Res, Comm.* 109: 348-354);

f) Tumor promoters (Huberman, E. and Callaham, M. F. (1979) *Proc. Natl. Acad. Sci.* (USA) 76: 1293-1297; Lottem, J. and Sachs, L. (1979) *Proc. Natl. Acad. Sci.* (USA) 76: 5158-5162); and g) inhibitors of DNA or RNA synthesis (Schwartz, E. L. and Sartorelli, A. C. (1982) *Cancer Res.* 42: 2651-2655, Terada, M., Epner, E., Nude!, U., Salmon, J., Fibach, E., Rifkind, R. A., and Marks, P. A. (1978) *Proc. Natl. Acad. Sci.* (USA) 75: 2795-2799; Morin, M. J. and Sartorelli, A. C. (1984) *Cancer Res* 44: 2807-2812; Schwartz, E. L., Brown, B. J., Nierenberg, M., Marsh, J. C., and Sartorelli, A. C. (1983) *Cancer Res.* 43: 2725-2730; Sugano, H., Furusawa, M., Kawaguchi, T., and Ikawa, Y. (1973) *Bibl. Hematol.* 39: 943-954; Ebert, P. S., Wars, I., and Buell, D. N. (1976) *Cancer Res.* 36: 1809-1813; Hayashi, M., Okabe, J., and Hozumi, M. (1979) Gann 70: 235-238).

A compound of the instant invention may also be useful for treating or preventing cancer in combination with γ-secretase inhibitors.

Also included in the scope of the claims is a method of treating cancer that comprises administering a therapeutically effective amount of a compound of Formula I in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γagonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

The compounds of the instant invention are useful in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris); Elliott's B Solution (Elliott's B Solution®); eltrombopag (Promacta®); epirubicin (Ellence®); Epoetin alfa (Epogen®); erlotinib (Tarceva®); estramustine (Emcyt®); etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrientm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar); temsirolimus (Torisel); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®); and zoledronate (Zometa®).

Non-limiting examples of other suitable anti-cancer agents for combination with the instant compounds are selected from the group consisting of a Cytostatic agent, Cisplatin, Deforolimus (described in PCT publication No. 2003/064383), Doxorubicin, liposomal doxorubicin (e.g., Caelyx®, Myocet®, Doxil®), Taxotere, Taxol, Etoposide, Irinotecan, Camptostar, Topotecan, Paclitaxel, Docetaxel, Epothilones, Tamoxifen, 5-Fluorouracil, Methoxtrexate, Temozolomide, cyclophosphamide, SCH 66336, R115777®, L778,123®, BMS 214662®, Iressa®, Tarceva®, Antibodies to EGFR, antibodies to IGFR (including, for example, those published in US 2005/0136063 published Jun. 23, 2005), ESK inhibitors, KSP inhibitors (such as, for example, those published in WO 2006/098962 and WO 2006/098961; ispinesib, SB-743921 from Cytokinetics), Centrosome associated protein E ("CENP-E") inhibitors (e.g., GSK-923295), Gleevec®, Intron, Ara-C, Adriamycin, Cytoxan, Gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6 Mercaptopurine, 6 Thioguanine, Fludarabine phosphate, Oxaliplatin, Leucovirin, ELOXATIN™, Vinblastine, Vincristine, Vindesine, Bleomycin, Dactinomycin, Daunorubicin, Doxorubicin, Epirubicin, Idarubicin, Mithramycin, Deoxycoformycin, Mitomycin C, L Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, bortezomib ("Velcade"), Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225®, Satriplatin, mylotarg, Avastin, Rituxan, Panitubimab, Sutent, Sorafinib, Sprycel (dastinib), Nilotinib, Tykerb (Lapatinib) and Campath.

In one embodiment, the invention provides a method of treating cancer, the method comprising administering an amount of a Pyrazolopyrrolopyrimidine or dipyrazolopyrimidine Compound or a pharmaceutically acceptable salt thereof, and an amount of one additional anticancer agent selected from the group consisting of Adriamycin, Altretamine, Amidox, Aminoglutethimide, Amsacrine, Anastrazole, Antibodies to EGFR, 3-AP, Aphidicolon, Ara-C, Arsenic trioxide, L Asparaginase, Bevacizumab, Bleomycin, BMS 214662, Bortezomib, Busulfan, Campath, Camptostar, Capecitabine, Carboplatin, Carmustine, Centrosome associated protein E ("CENP-E") inhibitors, Cetuximab, Cladribine, Chlorambucil, Chlormethine, Chlorotrianisene, Cisplatin, Clofarabine, cyclophosphamide, Cytarabine, a Cytostatic agent, Cytoxan, Dacarbazine, Dactinomycin, Daunorubicin, Dasatinib, Deforolimus, Deoxycoformycin, Didox, Diethylstilbestrol, Docetaxel, Doxorubicin, Dromostanolone, Droloxafine, Epirubicin, Epothilones, ERK inhibitors, Erlotinib, Etoposide, 17α-Ethinylestradiol, Estramustine, Exemestane, Floxuridine, Fludarabine, Fludarabine phosphate, 5-Fluorouracil, Fluoxymesterone, Flutamide, Fulvestrant, Gefitinib, Gemcitabine, Gemtuzumab ozogamcicin, Goserelin, GSK-923295, Hexamethylmelamine, Hydroxyprogesterone, Hydroxyurea, Ibritumomab Tiuxetan, Idarubicin, Ifosfamide, Imatinib mesylate, Intron, Irinotecan, ispinesib, KSP inhibitors, L778,123, Lapatinib, Leucovirin, Leuprolide, Lerozole, Letrazole, Levamisole, Liposomal Doxorubicin, Liposomal, Lomustine, Lonafarnib, Medroxyprogesteroneacetate, Megestrolacetate, Melphalan, 6 Mercaptopurine, Methoxtrexate, Methylprednisolone, Methyltestosterone, Mithramycin, Mitomycin C, Mitotane, Mitoxantrone, Navelbene, Nilotinib, Oxaliplatin, Paclitaxel, Panitubimab, Pentostatin, Pipobroman, Porfimer, Prednisolone, Prednisone propionate, Procarbazine, Reloxafine, Rituximab, Satriplatin, SB-743921, Sml1, Sorafinib, Streptozocin, Sunitinib, Tamoxifen, Taxotere, Taxol, Temozolomide, Teniposide, Testolactone, Testosterone, Tezacitabine, 6 Thioguanine, Thiotepa, Tipifarnib, Topotecan, Toremifene, Tositumomab, Trastuzumab, Triamcinolone, Triapine, Triethylenemelamine, Triethylenethiophosphoramine, Trimidox, Uracil mustard, Vinblastine, Vincristine, Vindesine, and Vinorelbine.

In one embodiment, the invention provides a method of treating cancer, the method comprising administering an amount of a Pyrazolopyrrolopyrimidine or dipyrazolopyrimidine Compound or a pharmaceutically acceptable salt thereof, and an amount of one or more of a MAP Kinase pathway inhibitor such as bRaf, MEK, or ERK inhibitors to a patient in need thereof.

In another embodiment, the invention provides a method of treating cancer, the method comprising administering an amount of a Pyrazolopyrrolopyrimidine or dipyrazolopyrimidine Compound or a pharmaceutically acceptable salt thereof, and an amount of one or more of ERK inhibitors (for example, compounds described in WO2008/156739, WO2007/070398, WO 2008/156739 and US publication 2007/0232610) to a patient in need thereof.

In one embodiment, the invention provides a method of treating cancer, the method comprising administering an amount of a Pyrazolopyrrolopyrimidine or dipyrazolopyrimidine Compound or a pharmaceutically acceptable salt thereof, and an amount of one or more of an anti-IGF-1R antibody. Specific anti-IGF-1R antibodies include, but are not limited to, dalotuzumab, figitumumab, cixutumumab, SHC 717454, Roche R1507, EM164 or Amgen AMG479.

The instant invention also includes a pharmaceutical composition useful for treating or preventing cancer that comprises a therapeutically effective amount of a compound of Formula I and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs) and an agent that interferes with a cell cycle checkpoint.

The use of all of these approaches in combination with the instant compounds described herein are within the scope of the present invention.

Compositions and Administration

This invention is also directed to pharmaceutical compositions which comprise at least one Pyrazolopyrrolopyrimidine or dipyrazolopyrimidine Compound, or a pharmaceutically acceptable salt of said compound and at least one pharmaceutically acceptable carrier.

When administered to a patient, the Pyrazolopyrrolopyrimidine or dipyrazolopyrimidine Compounds can be administered as a component of a composition that comprises a pharmaceutically acceptable carrier or vehicle. The present invention provides pharmaceutical compositions comprising an effective amount of at least one Pyrazolopyrrolopyrimidine or dipyrazolopyrimidine Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

The Pyrazolopyrrolopyrimidine or dipyrazolopyrimidine Compounds of the present invention may also be delivered transdermally. The transdermal compositions can take the form of creams, lotions, aerosols and/or emulsions and can be included in a transdermal patch of the matrix or reservoir type as are conventional in the art for this purpose.

Additionally, the compositions of the present invention may be formulated in sustained release form to provide the rate controlled release of any one or more of the components or active ingredients to optimize therapeutic effects, i.e., anticancer activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the Pyrazolopyrrolopyrimidine or dipyrazolopyrimidine Compound is administered orally.

In another embodiment, the Pyrazolopyrrolopyrimidine or dipyrazolopyrimidine Compound is administered intravenously.

In another embodiment, the Pyrazolopyrrolopyrimidine or dipyrazolopyrimidine Compound is administered topically.

In still another embodiment, the Pyrazolopyrrolopyrimidine or dipyrazolopyrimidine Compounds is administered sublingually.

In one embodiment, a pharmaceutical preparation comprising at least one Pyrazolopyrrolopyrimidine or dipyrazolopyrimidine Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Pyrazolopyrrolopyrimidine or dipyrazolopyrimidine Compound(s) by weight or volume. In various embodiments, the present compositions can contain, in one embodiment, from about 1% to about 70% or from about 5% to about 60% of the Pyrazolopyrrolopyrimidine or dipyrazolopyrimidine Compound(s) by weight or volume.

The quantity of Pyrazolopyrrolopyrimidine or dipyrazolopyrimidine Compound in a unit dose of preparation may be varied or adjusted from about 0.1 mg to about 5000 mg. In various embodiments, the quantity is from about 10 mg to about 5000 mg, about 10 mg to about 1000 mg, 1 mg to about 500 mg, 1 mg to about 100 mg, and 1 mg to about 50 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

For administration to human patients, the amount and frequency of administration of the Pyrazolopyrrolopyrimidine or dipyrazolopyrimidine Compounds will be regulated according to the judgment of the attending clinician considering such factors as age, condition and size of the patient as well as severity of the symptoms being treated. Generally, a total daily dosage of the Pyrazolopyrrolopyrimidine or dipyrazolopyrimidine Compounds range from about 0.1 to about 5000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 5000 mg/day, administered in a single dose or in 2-4 divided doses. In another embodiment, the dosage is from about 100 to about 5000 mg/day, administered in a single dose or in 2-4 divided doses. In still another embodiment, the dosage is from about 500 to about 5000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Pyrazolopyrrolopyrimidine or dipyrazolopyrimidine Compound or a pharmaceutically acceptable salt thereof; (ii) one or more additional therapeutic agents that are not a Pyrazolopyrrolopyrimidine or dipyrazolopyrimidine Compound; and (iii) a pharmaceutically acceptable carrier, wherein the amounts in the composition are together effective to treat disease or disorder associated with dysregulated mTOR activity, such as a cancer.

In Vitro and In Vivo Methods:

The present invention also provides methods of using the pyrazolopyrrolopyrimidine or dipyrazolopyrimidine compounds of the present invention for inducing terminal differentiation, cell growth arrest and/or, apoptosis of neoplastic cells thereby inhibiting the proliferation of such cells. The methods can be practiced in vivo or in vitro.

In one embodiment, the present invention provides in vitro methods for selectively inducing terminal differentiation, cell growth arrest and/or apoptosis of neoplastic cells, thereby inhibiting proliferation of such cells, by contacting the cells with an effective amount of any one or more of the pyrazolopyrrolopyrimidine or dipyrazolopyrimidine compounds described herein.

In a particular embodiment, the present invention relates to an in vitro method of selectively inducing terminal differentiation of neoplastic cells and thereby inhibiting proliferation of such cells. The method comprises contacting the cells under suitable conditions with an effective amount of one or more of the pyrazolopyrrolopyrimidine compounds described herein.

In another embodiment, the invention relates to an in vitro method of selectively inducing cell growth arrest of neoplastic cells and thereby inhibiting proliferation of such cells. The method comprises contacting the cells under suitable conditions with an effective amount of one or more of the pyrazolopyrrolopyrimidine or dipyrazolopyrimidine compounds described herein.

In another embodiment, the invention relates to an in vitro method of selectively inducing apoptosis of neoplastic cells and thereby inhibiting proliferation of such cells. The method comprises contacting the cells under suitable conditions with an effective amount of one or more of the pyrazolopyrrolopyrimidine or dipyrazolopyrimidine compounds described herein.

In another embodiment, the invention relates to an in vitro method of inducing terminal differentiation of tumor cells in a tumor comprising contacting the cells with an effective amount of any one or more of the pyrazolopyrrolopyrimidine or dipyrazolopyrimidine compounds described herein.

Although the methods of the present invention can be practiced in vitro, it is contemplated that the preferred embodiment for the methods of selectively inducing terminal differentiation, cell growth arrest and/or apoptosis of neoplastic cells, and of inhibiting mTor will comprise contacting the cells in vivo, i.e., by administering the compounds to a subject harboring neoplastic cells or tumor cells in need of treatment.

Thus, the present invention provides in vivo methods for selectively inducing terminal differentiation, cell growth arrest and/or apoptosis of neoplastic cells in a subject, thereby inhibiting proliferation of such cells in the subject, by administering to the subject an effective amount of any one or more of the pyrazolopyrrolopyrimidine or dipyrazolopyrimidine compounds described herein.

In a particular embodiment, the present invention relates to a method of selectively inducing terminal differentiation of neoplastic cells and thereby inhibiting proliferation of such cells in a subject. The method comprises administering to the subject an effective amount of one or more of the pyrazolopyrrolopyrimidine or dipyrazolopyrimidine compounds described herein.

In another embodiment, the invention relates to a method of selectively inducing cell growth arrest of neoplastic cells and thereby inhibiting proliferation of such cells in a subject. The method comprises administering to the subject an effective amount of one or more of the pyrazolopyrrolopyrimidine or dipyrazolopyrimidine compounds described herein.

In another embodiment, the invention relates to a method of selectively inducing apoptosis of neoplastic cells and thereby inhibiting proliferation of such cells in a subject. The method comprises administering to the subject an effective amount of one or more of the pyrazolopyrrolopyrimidine or dipyrazolopyrimidine compounds described herein.

In another embodiment, the invention relates to a method of treating a patient having a tumor characterized by proliferation of neoplastic cells. The method comprises administering to the patient one or more of the pyrazolopyrrolopyrimidine or dipyrazolopyrimidine compounds described herein. The amount of compound is effective to selectively induce terminal differentiation, induce cell growth arrest and/or induce apoptosis of such neoplastic cells and thereby inhibit their proliferation.

Kits

Another aspect of this invention is a kit comprising a therapeutically effective amount of at least one Pyrazolopyrrolopyrimidine or dipyrazolopyrimidine Compound, or a pharmaceutically acceptable salt of said compound, and a pharmaceutically acceptable carrier, vehicle or diluent.

Yet another aspect of this invention is a kit comprising an amount of at least one Pyrazolopyrrolopyrimidine or dipyrazolopyrimidine Compound, or a pharmaceutically acceptable salt of said compound and an amount of at least one additional anti-cancer agent listed above, wherein the amounts of the two or more active ingredients result in a desired therapeutic effect. In one embodiment, the at least one Pyrazolopyrrolopyrimidine or dipyrazolopyrimidine Compound and the at least one additional anti-cancer agent are provided in the same container. In one embodiment, the at least one Pyrazolopyrrolopyrimidine or dipyrazolopyrimidine Compound and the at least one additional anti-cancer agent are provided in separate containers.

The invention is illustrated in the examples in the Experimental Details Section that follows. This section is set forth to aid in an understanding of the invention but is not intended to, and should not be construed to limit in any way the invention as set forth in the claims which follow thereafter.

Experimental Details Section

Solvents, reagents, and intermediates that are commercially available were used as received. Reagents and intermediates that are not commercially available were prepared in the manner as described below. $^1$H NMR spectra were obtained on a Varian spectrometer (400 MHz and 500 MHz) are reported as ppm down field from Me$_4$Si with number of protons, multiplicities, and coupling constants, in Hertz indicated parenthetically. Where LC/MS data are presented, analyses was performed using an Agilent 1100 Series LC w/MicroMass Quattro MS Varian Pursuit XRs C18, 5 micron, 150 mm×4.6 mm ID gradient flow (0.1% TFA or 0.2% FA): 0 min-5% ACN, 7.5 min-100% ACN, 8.5 min-100 ACN, 8.51 min-5% ACN, 10 min-stop 3 ml/min. The retention time and observed parent ion are given. Where the description indicates the reaction mixture was purified by HPLC, the description refers to using a preparative Agilent 1100 Series LC/MSD SL system: Column Reverse Phase-Varian Pursuit XRs 10□C-18 250×21.2 mm; elution with gradient Acetonitrile/water with 0.1% TFA or 0.2% formic acid. The desired product was detected and collected by a mass-triggered automatic sample collector. Flash column chromatography was performed using pre-packed normal phase silica from Biotage, Inc.

The following solvents, reagents and reaction conditions may be referred to by their abbreviations:
Aq: aqueous
g or gm: grams
psi: pounds per square inch
pH: concentration of hydronium ions in a solution
° C.: degrees Celsius
h: hours
THF: Tetrahydrofuran
Et$_2$O: diethyl ether
SEM: 2-(trimethylsilyl)ethoxymethyl
LC-MS: Liquid chromatography mass spectrometry
DCM: dichloromethane
N: Normal
ml: milliliter
NBS: N-Bromosuccinimide
NCS: N-Chlorosuccinimide
NIS: N-iodosuccinimide
r.t.: room temperature
MeOH: methanol
DIEA: diisopropylethylamine
EtOAc: ethyl acetate
EtOH: ethanol
DMF: dimethylformamide
wt %: weight percent
m/z: mass per charge
LiOH: lithium hydroxide
DMSO: dimethylsulfoxide
HPLC: high performance liquid chromatography
IPA: isopropanol
Ret: retention
Rt: retention time
RP: reverse phase
ACN: acetonitrile
CH$_3$CN: acetonitrile
MeCN: acetonitrile
MeI: iodomethane
r.t.: room temperature
pTSA: para-toluene sulfonic acid
CDI: N,N'-carbonyldiimidazole
mg: milligram
PMA: phosphomolybdic acid
LiHMDS: Lithium bis(trimethylsilyl)amide
HMDS: hexamethyldisilazane
Pd/C: palladium on carbon
H2: hydrogen gas
PdCl$_2$(dppf): [1,1'-bis(diphenylphosphino)ferrocene]dichloropalladium(II)
μmol: micromole
TFA: trifluoroacetic acid
NMP: N-methyl-2-pyrrolidone
min: minute
DME: dimethylethane
AcOH: acetic acid
BBN: 9-borabicyclo[3.3.1]nonane
BOC: tertiary-butyloxycarbonyl
M: Molar
mmol: millimolar
DIEA: diisopropylethylamine
Bu3SnCN: tributyltin cyanide
Pd[P(t-Bu)$_3$]$_2$: bis(tributyl)Phosphine) palladium
Pd(PPh$_3$)$_4$: tetrakis(triphenylphosphine) palladium
EDCI: 1-ethyl-3-(3-dimethylaminopropyl)-carbodiimide
UV: ultraviolet
LDA: lithium diisopropylamide
Tf: trifluoromethanesulfonyl

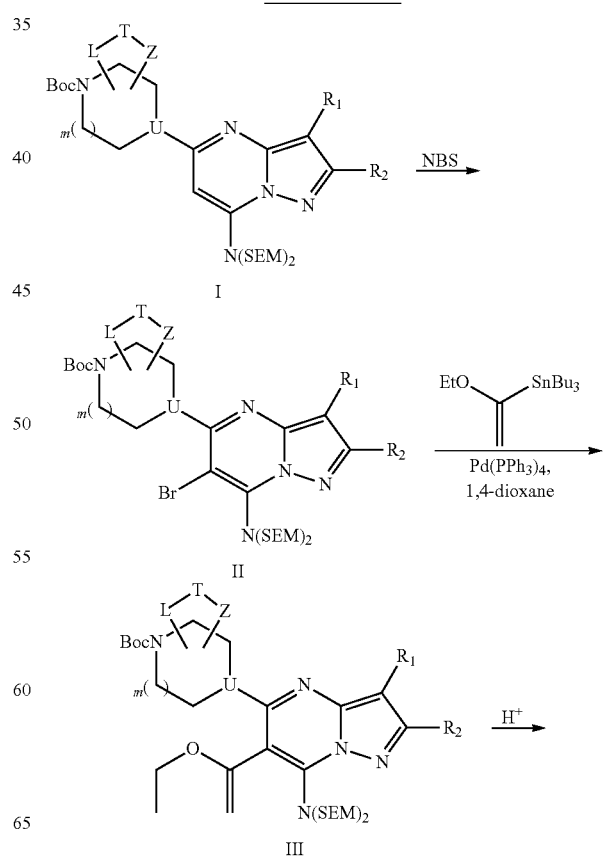

General Scheme 1

-continued

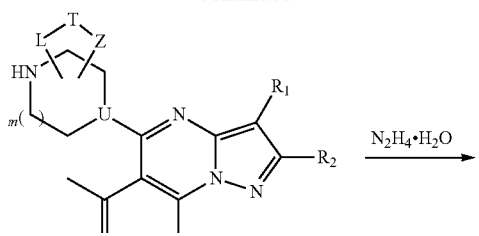

IV

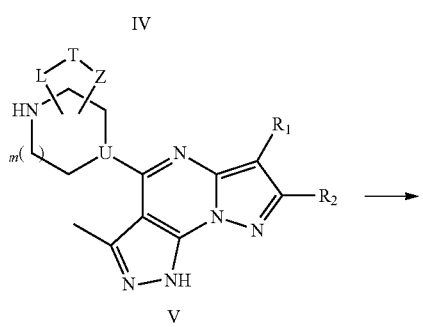

V

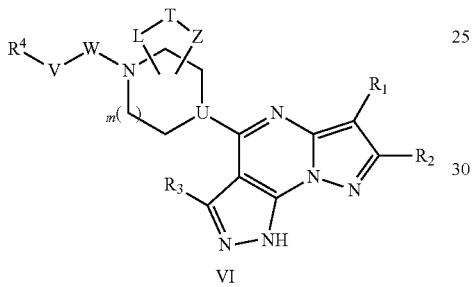

VI

-continued

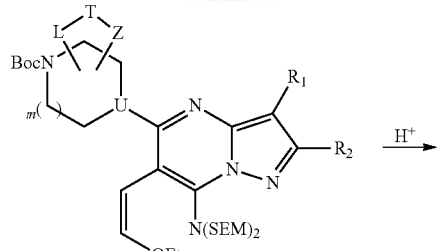

VII

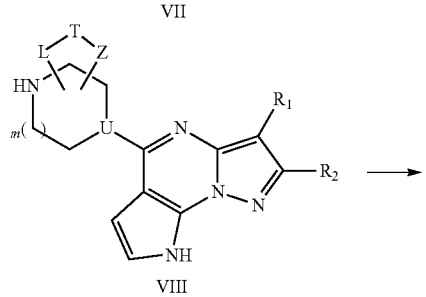

VIII

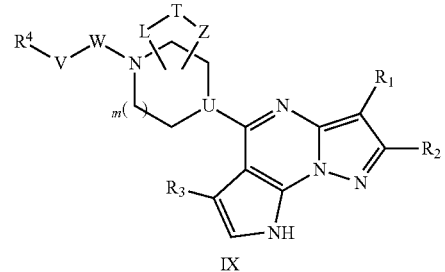

IX

Substituted pyrazolo[1,5-a]pyrimidine I is brominated by reacting with N-Bromosuccinimide (NBS) at room temperature in an appropriate solvent or solvent mixture such as DCM, DCM-CH$_3$CN and DMF to provide the corresponding bromide intermediate II (General Scheme 1). Bromide intermediate II is heated with tributyl (1-ethoxyvinyl)stannane in an appropriate solvent or solvent mixture such as 1,4-dioxane at or around 100° C., in the presence of an appropriate catalyst such as Pd(PPh$_3$)$_4$, to afford the corresponding enol ether intermediate III. Enol ether intermediate III is treated with an appropriate acid, such as TFA in H$_2$O, to afford the corresponding intermediate IV. Intermediate IV is treated with hydrazine to afford the corresponding intermediate V. Intermediate V is transferred to compound VI.

Bromide intermediate II is heated with (Z)-tributyl(2-ethoxyvinyl)stannane in an appropriate solvent or solvent mixture such as 1,4-dioxane, 1,4-dioxane-CH$_3$CN, at or around 100° C., in the presence of an appropriate catalyst such as Pd(PPh$_3$)$_4$, to afford the corresponding enol ether intermediate VII (General Scheme 2). Enol ether intermediate VII is treated with an appropriate acid, such as TFA in H$_2$O, to afford the corresponding intermediate VIII. Intermediate VIII is transferred to compound IX.

EXAMPLE 1

Preparation of ((1R,3s,5S)-3-(3-methyl-6-(6-phenylpyridin-3-yl)-1H-dipyrazolo[1,5-a:4',3'-e]pyrimidin-4-yl)-8-azabicyclo[3.2.1]octan-8-yl)(4H-1,2,4-triazol-3-yl)methanone Step 1: Preparation of pyrazolo[1,5-a]pyrimidine-5,7-diol General Scheme 2

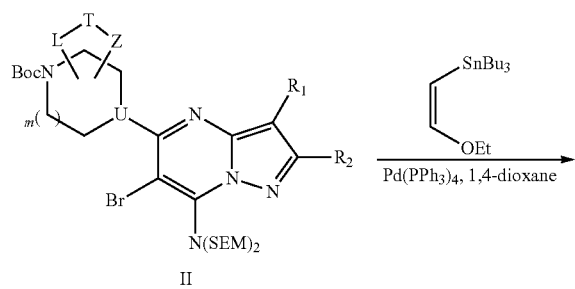

II

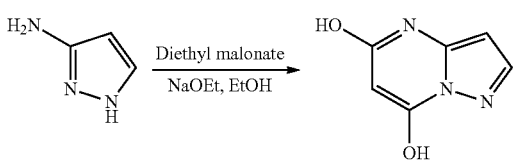 [SMILES: Nc1cc[nH]n1 ; Oc1cc(O)n2nccc2n1]

To 1H-pyrazol-3-amine (12.3 g, 148.0 mmol) in EtOH (50 mL) was added diethyl malonate (25.0 mL, 164.7 mmol), 21 wt % NaOEt in EtOH (110 mL, 294.6 mmol) and additional EtOH (50 mL). The resulting mixture was then heated at 80° C. under an atmosphere of argon for 16 hours, at which time the reaction was allowed to cool to room temperature. The reaction mixture was then concentrated in vacuo until almost dry, before H$_2$O (500 mL) was added. Vigorous stirring aided the dissolving of solids, at which time conc. HCl was added until pH~2 was attained (solid precipitate formed). The precipitate was collected and dried by vacuum filtration giving pyrazolo[1,5-a]pyrimidine-5,7-diol as a tan solid.

Step 2: Preparation of
5,7-dichloropyrazolo[1,5-a]pyrimidine

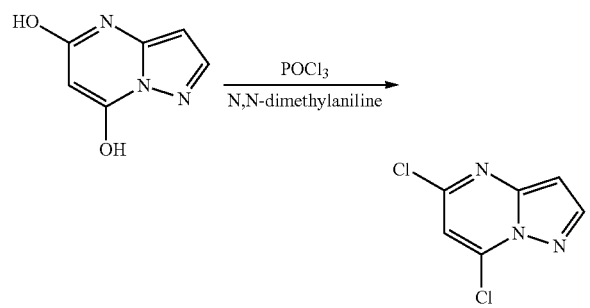

To pyrazolo[1,5-a]pyrimidine-5,7-diol (9.6 g, 63.5 mmol) in a 500 mL flask was added POCl$_3$ (125 mL, 1341.1 mmol). The flask was then cooled to 0° C. and N,N-dimethylaniline (22 mL, 173.6 mmol) was carefully added. On warming to room temperature, the reaction was then heated at 60° C. under an atmosphere of argon for 16 hours. On cooling, the reaction mixture was concentrated in vacuo to give a brown viscous liquid. This brown viscous liquid was carefully poured onto ice and allowed to warm to room temperature overnight. To the brown solution was carefully added saturated NaHCO$_3$ solution until no further effervescence was observed and pH ~8 was attained. Organics were then extracted with CH$_2$Cl$_2$ (4×50 mL), dried (Na$_2$SO$_4$) and concentrated in vacuo to give a brown liquid. Gradient column chromatography on silica eluting with 50% CH$_2$Cl$_2$/hexanes (to elute aniline) followed by 75% CH$_2$Cl$_2$/hexanes (to elute product) gave 5,7-dichloropyrazolo[1,5-a]pyrimidine as a white solid.

Step 3: Preparation of
5-chloropyrazolo[1,5-a]pyrimidin-7-amine

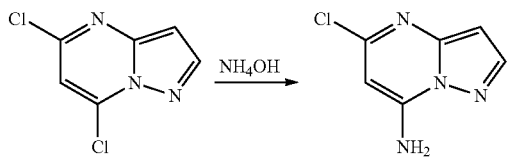

To 5,7-dichloropyrazolo[1,5-a]pyrimidine (7.6 g, 40.4 mmol) in a sealed vessel was added NH$_4$OH (100 mL). The vessel was then sealed and heated at 85° C. for 2.5 hours, at which time the consistency of the white solid had changed (from foamy white solid to free-flowing white solid). The vessel was removed from the heat source and allowed to cool to room temperature overnight. On cooling, the contents of the vessel were collected and dried by vacuum filtration giving 5-chloropyrazolo[1,5-a]pyrimidin-7-amine as a yellow-tinged white solid.

Step 4: Preparation of 5-chloro-N,N-bis ((2-(trimethylsilyl)ethoxy)methyl)pyrazolo[1,5-a]pyrimidin-7-amine

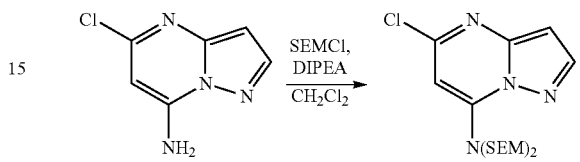

To 5-chloropyrazolo[1,5-a]pyrimidin-7-amine (6.7 g, 39.7 mmol) in CH$_2$Cl$_2$ (30 mL) was added N,N-diisopropylethylamine (48.0 mL, 275.6 mmol) followed by 2-(trimethylsilyl)ethoxymethyl chloride (25.0 mL, 141.7 mmol). The reaction was heated at 45° C. for 3 hours before being allowed to cool to room temperature. The reaction mixture was then poured into a separatory funnel containing ~100 mL saturated NaHCO$_3$ solution and CH$_2$Cl$_2$ (50 mL). Organics were then extracted with CH$_2$Cl$_2$ (4×50 mL), dried (Na$_2$SO$_4$) and concentrated in vacuo to give a thick orange liquid (33.8 g). Gradient column chromatography on silica eluting with 5% to 15% EtOAc/hexanes gave crude 5-chloro-N,N-bis((2-(trimethylsilyl)ethoxy)methyl)pyrazolo[1,5-a]pyrimidin-7-amine as a colorless liquid.

Step 5: Preparation of tert-butyl 3-(trifluoromethylsulfonyloxy)-8-azabicyclo[3.2.1]oct-3-ene-8-carboxylate

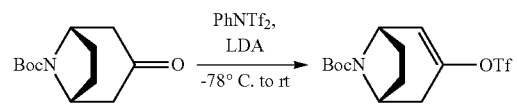

To a solution of N-Boc-nortropinone (6 g, 26.6 mmol) in THF (70 ml) at −78° C. was added LDA (2 M in haptane/THF/ethyl benzene, 20 ml, 40 mmol) slowly and the reaction mixture was stirred for 10 min. A solution of N-phenylbis(trifluoromethanesulfonimide) (10.5 g, 29.3 mmol) in THF (48 ml) was added. The reaction mixture was stirred at −78° C. for 30 min and the cooling bath was removed to warm it up to room temperature for 1.5 h until all N-Boc-nortropinone was utilized. Saturated NH$_4$Cl solution (~10 mL) was added and stirring was continued for 5 minutes before the reaction mixture was transferred to a separatory funnel using EtOAc (150 mL). The organics were then extracted with EtOAc (2×125 ml), and washed with water (2×30 ml), brine (1×30 ml), and dried over MgSO$_4$. The solvent was removed in vacuo and the residue was purified by column chromatography on silica gel. Elution with EtOAc/Hexanes (0-35%) gave the desired product, tert-butyl 3-(trifluoromethylsulfonyloxy)-8-azabicyclo[3.2.1]oct-3-ene-8-carboxylate.

Step 6: Preparation of tert-butyl 3-(4,4,5,5-tetramethyl-1,3,2-dioxaborolan-2-yl)-8-azabicyclo[3.2.1]oct-2-ene-8-carboxylate

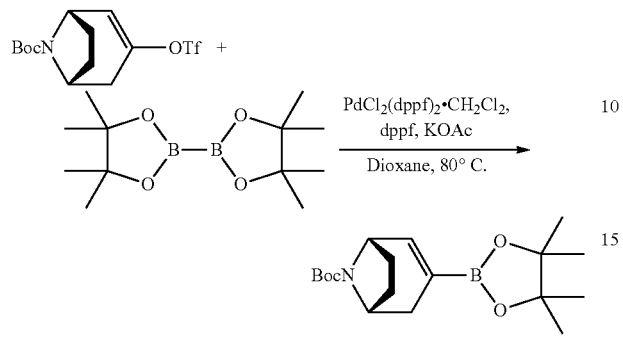

A mixture of tert-butyl 3-(trifluoromethylsulfonyloxy)-8-azabicyclo[3.2.1]oct-3-ene-8-carboxylate (10.1 g, 28.4 mmol), bis(pinacolato)diboron (8.7 g, 34.1 mmol), KOAc (8.4 g, 85.3 mmol), PdCl$_2$(dppf)$_2$·CH$_2$Cl$_2$ (1.4 g, 1.7 mmol), and dppf (1 g, 1.8 mmol) in dioxane (170 ml) was flushed with argon and stirred at 80° C. for 16 h. On cooling, the solvent was evaporated, and the crude residue was redissolved in EtOAc (500 ml), washed with water (1×125 ml), brine (1×125 ml), and dried over MgSO$_4$. The solvent was removed in vacuo and the residue was purified by column chromatography on silica gel. Elution with EtOAc/Hexanes (0-40%) gave the desired product, tert-butyl 3-(4,4,5,5-tetramethyl-1,3,2-dioxaborolan-2-yl)-8-azabicyclo[3.2.1]oct-2-ene-8-carboxylate.

Step 7: Preparation of tert-butyl 3-(7-(bis((2-(trimethylsilyl)ethoxy)methyl)amino)pyrazolo[1,5-a]pyrimidin-5-yl)-8-azabicyclo[3.2.1]oct-2-ene-8-carboxylate

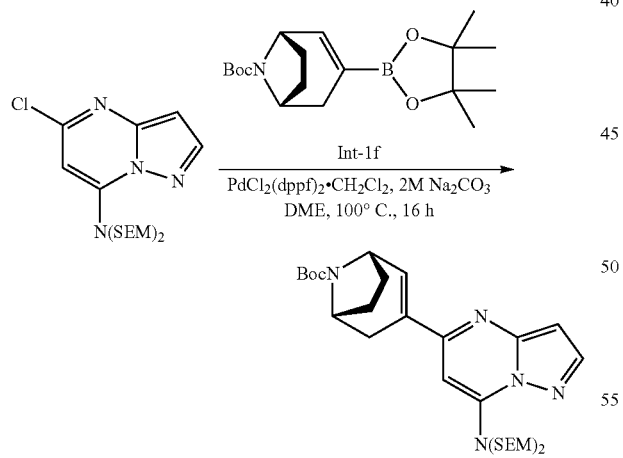

To 5-chloro-N,N-bis((2-(trimethylsilyl)ethoxy)methyl)pyrazolo[1,5-a]pyrimidin-7-amine (11.1 g, 25.8 mmol) in DME (200 mL) was added tert-butyl 3-(4,4,5,5-tetramethyl-1,3,2-dioxaborolan-2-yl)-8-azabicyclo[3.2.1]oct-2-ene-8-carboxylate (9.5 g, 28.4 mmol), PdCl$_2$(dppf)$_2$ (2.1 g, 2.6 mmol) and 2M Na$_2$CO$_3$ (100 ml). The reaction was heated at 100° C. for 16 hours, at which time LC/MS analysis confirmed full consumption of starting material. On cooling, H$_2$O (80 ml) and EtOAc (200 ml) were added and the organics were extracted with EtOAc (2×250 ml), dried (Na$_2$SO$_4$) and concentrated in vacuo to give a crude product. Gradient column chromatography on silica eluting with 10% to 60% EtOAc/hexanes(0-50%) gave tert-butyl 3-(7-(bis((2-(trimethylsilyl)ethoxy)methyl)amino)pyrazolo[1,5-a]pyrimidin-5-yl)-8-azabicyclo[3.2.1]oct-2-ene-8-carboxylate.

Step 8: Preparation of anti & syn—tert-butyl 3-(7-(bis((2-(trimethylsilyl)ethoxy)methyl)amino)pyrazolo[1,5-a]pyrimidin-5-yl)-8-azabicyclo[3.2.1]oct-2-ene-8-carboxylate

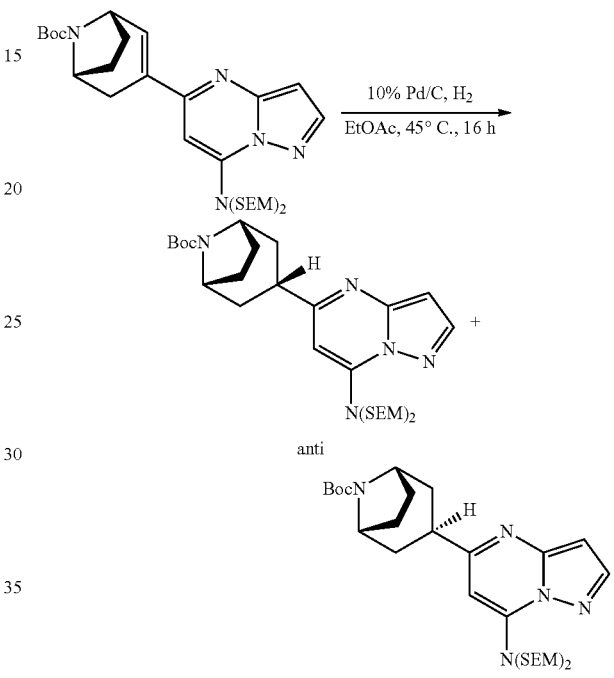

A mixture of tert-butyl 3-(7-(bis((2-(trimethylsilyl)ethoxy)methyl)amino)pyrazolo[1,5-a]pyrimidin-5-yl)-8-azabicyclo[3.2.1]oct-3-ene-8-carboxylate (12.2 g, 20.3 mmol), 10% Pd/C (2.1 g) in EtOAc (175 ml) was stirred at 45° C. under hydrogen (balloon pressure) for 16 hours. After filtration and concentration, the crude mixture of two isomers was purified by gradient column chromatography on silica eluting with EtOAc/Hexanes (0-35%) to give the slightly impure "syn" product and the "anti" product which was used in the following reaction sequences.

Step 9: Preparation of tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate

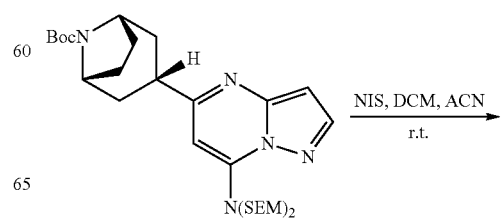

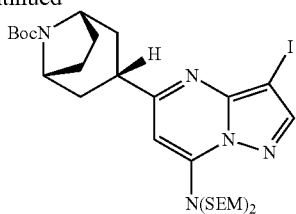

To the "anti" tert-butyl 3-(7-(bis((2-(trimethylsilyl)ethoxy)methyl)amino)pyrazolo[1,5-a]pyrimidin-5-yl)-8-azabicyclo[3.2.1]octane-8-carboxylate (6.04 g, 10 mmol) in CH₃CN (40 mL) and DCM (40 mL) was added N-iodosuccinimide (2.5 g, 11 mmol) portionwise and the resulting mixture was stirred at room temperature for 1.5 h, at which time LC/MS confirmed full conversion of starting material to product. The solvent was removed in vacuo and the residue was purified by column chromatography on silica gel. Elution with EtOAc/Hexanes (0-50%) gave tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate.

Step 10: Preparation of tert-butyl 3-(7-(bis((2-(trimethylsilyl)ethoxy)methyl)amino)-3-(6-phenylpyridin-3-yl)pyrazolo[1,5-a]pyrimidin-5-yl)-8-azabicyclo[3.2.1]octane-8-carboxylate

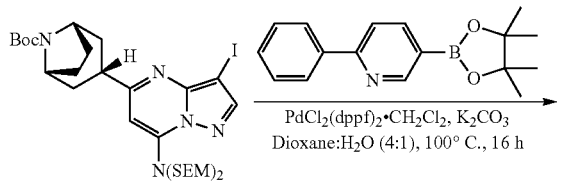

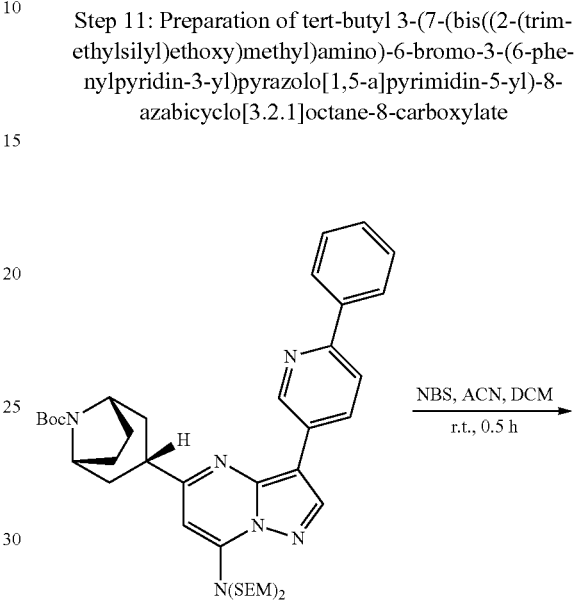

To tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (2 g, 2.7 mmol) in dioxane (22 mL) and H₂O (5.5 mL) was added 2-phenyl-5-(4,4,5,5-tetramethyl-1,3,2-dioxaborolan-2-yl)pyridine (1.2 g, 4.1 mmol), PdCl₂(dppf)·CH₂Cl₂ (0.3 g, 0.3 mmol) and K₂CO₃ (1.2 g, 8.2 mmol). The reaction was heated at 100° C. for 15 hours, at which time LC/MS analysis confirmed full consumption of starting material. On cooling, H₂O (40 ml) and EtOAc (100 mL) were added and organics were extracted with EtOAc (2×75 ml), dried (Na₂SO₄) and concentrated in vacuo to crude. Gradient column chromatography on silica eluting with 0 to 50% EtOAc/hexanes gave tert-butyl 3-(7-(bis((2-(trimethylsilyl)ethoxy)methyl)amino)-3-(6-phenylpyridin-3-yl)pyrazolo[1,5-a]pyrimidin-5-yl)-8-azabicyclo[3.2.1]octane-8-carboxylate.

Step 11: Preparation of tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-8-azabicyclo[3.2.1]octane-8-carboxylate

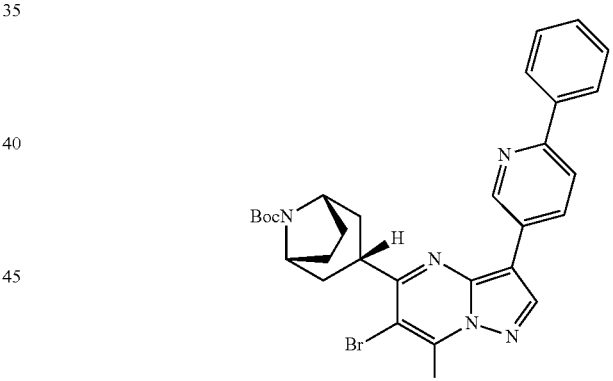

To a mixture of tert-butyl 3-(7-(bis((2-(trimethylsilyl)ethoxy)methyl)amino)-3-(6-phenylpyridin-3-yl)pyrazolo[1,5-a]pyrimidin-5-yl)-8-azabicyclo[3.2.1]octane-8-carboxylate (1.7 g, 2.3 mmol) in CH₃CN (10 mL) and dichloromethane (10 mL) was added N-bromosuccinimide (0.45 g, 2.5 mmol) portionwise and the resulting mixture was stirred at room temperature for 0.5 h, at which time LC/MS confirmed full conversion of starting material to product. The solvent was removed in vacuo and the residue was purified by column chromatography on silica gel. Elution with EtOAc/Hexanes (0-50%) gave tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-8-azabicyclo[3.2.1]octane-8-carboxylate.

47

Step 12: Preparation of tert-butyl 3-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-8-azabicyclo[3.2.1]octane-8-carboxylate

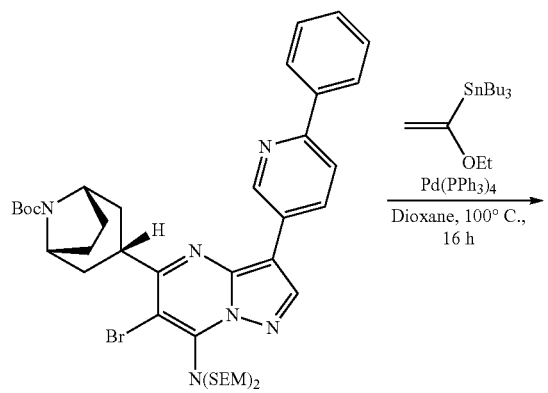

A mixture of compound tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-8-azabicyclo[3.2.1]octane-8-carboxylate (834 mg, 0.49 mmol), tributyl(1-ethoxyvinyl)tin (356 mg, 0.98 mmol), tetrakis(triphenylphosphine)palladium (56.9 mg, 0.049 mmol) in dioxane (6 mL) was degassed with argon for five minutes. It was then heated at 100° C. in a sealed tube for 16 h, at which time LC/MS analysis confirmed full consumption of starting material. On cooling, the solvent was rotoevaporated, and the crude residue was redissolved in EtOAc, washed with 0.5 M KF solution, brine (1×25 mL), and dried over MgSO$_4$. The solvent was removed in vacuo and the residue was purified by column chromatography on silica gel. Elution with EtOAc/Hexanes gave tert-butyl 3-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-8-azabicyclo[3.2.1]octane-8-carboxylate.

48

Step 13: Preparation of 1-(7-Amino-5-(-8-azabicyclo[3.2.1]octan-3-yl)-3-(6-phenylpyridin-3-yl)pyrazolo[1,5-a]pyrimidin-6-yl)ethanone

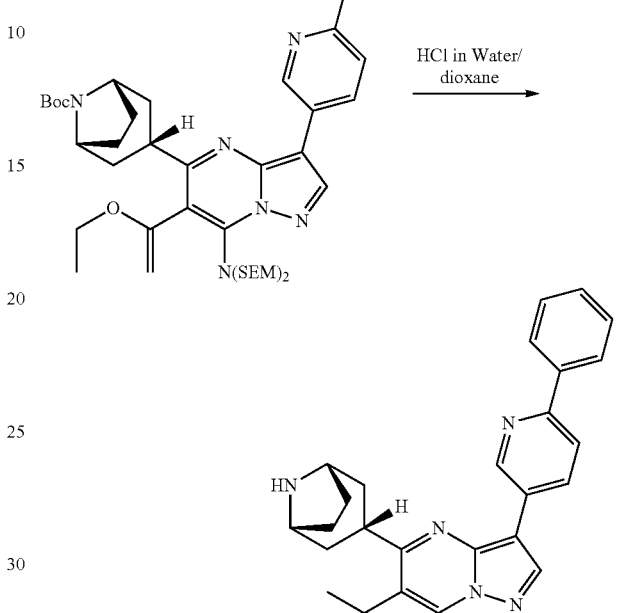

To a mixture of tert-butyl 3-(7-(bis((2-(trimethylsilyl)ethoxy)methyl)amino)-6-(1-ethoxyvinyl)-3-(6-phenylpyridin-3-yl)pyrazolo[1,5-a]pyrimidin-5-yl)-8-azabicyclo[3.2.1]octane-8-carboxylate (1.1 g, 1.3 mmol) in dioxane (7 mL) was added 4 M HCl in water (2.6 ml) at 0° C. After stirring for 10 min at 0° C., 4 M HCl in dioxane (2.6 mL) was added. The reaction mixture was stirred at 0° C. for 30 min and the cooling bath was removed to warm it up to room temperature for 15 h, at which time LC/MS analysis confirmed full consumption of starting material. The solvent was removed in vacuo to get the desired product as an HCl salt.

Step 14: Preparation of ((1R,3s,5S)-3-(3-methyl-6-(6-phenylpyridin-3-yl)-1H-dipyrazolo[1,5-a:4',3'-e]pyrimidin-4-yl)-8-azabicyclo[3.2.1]octan-8-yl)(4H-1,2,4-triazol-3-yl)methanone

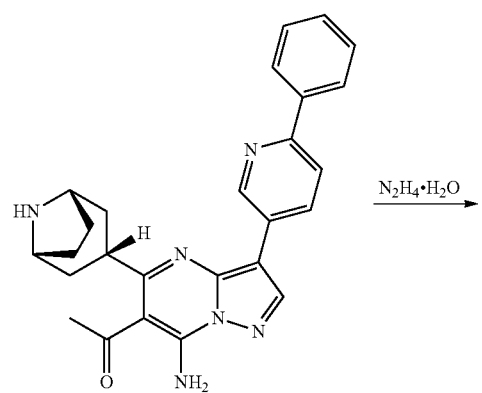

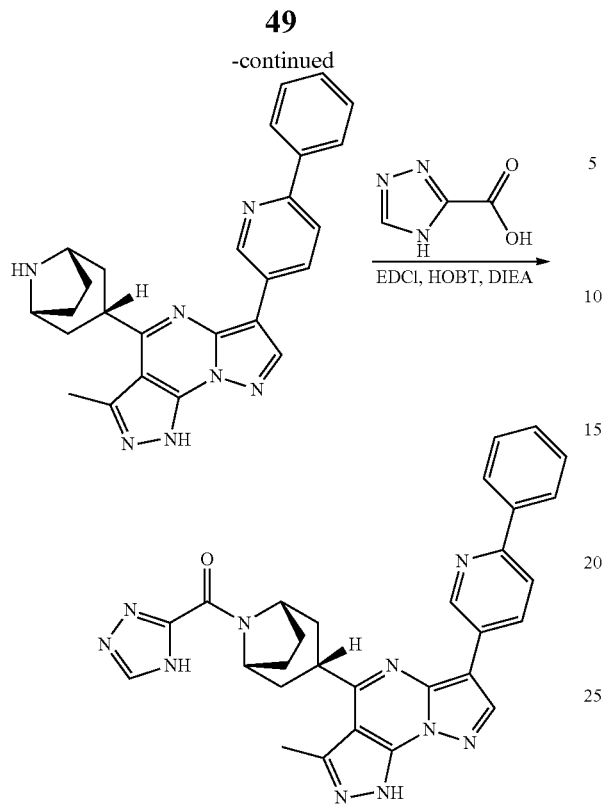

A mixture of 1-(7-Amino-5-(-8-azabicyclo[3.2.1]octan-3-yl)-3-(6-phenylpyridin-3-yl)pyrazolo[1,5-a]pyrimidin-6-yl)ethanone (131.4 mg, 0.30 mmol), $N_2H_4 \cdot H_2O$ (150 ul, 3.0 mmol) in NMP (10 ml) was heated first at 100° C. for 30 min and then at 200° C. for 60 min under microwave condition. The mixture was put on rotovap and concentrated at 60° C. for 2 h to remove excess $N_2H_4 \cdot H_2O$. 1H-1,2,4-triazole-3-carboxylic acid (101.7 mg, 0.90 mmol), EDC (229 mg, 1.20 mmol), HOBt (121.5 mg, 0.90 mmol) and DIEA (521.6 uL, 3.0 mmol) were then added and the mixture was stirred at room temperature for 1 h. Purification with prep-LC provided ((1R,3s,5S)-3-(3-methyl-6-(6-phenylpyridin-3-yl)-1H-dipyrazolo[1,5-a:4',3'-e]pyrimidin-4-yl)-8-azabicyclo[3.2.1]octan-8-yl)(4H-1,2,4-triazol-3-yl)methanone.

| # | Structures | Compound Name | M + H (calculated)/ M + H (observed) | pAKT S473 IC50 | p4E-BP1 Thr37/46 IC50 |
|---|---|---|---|---|---|
| 1 | 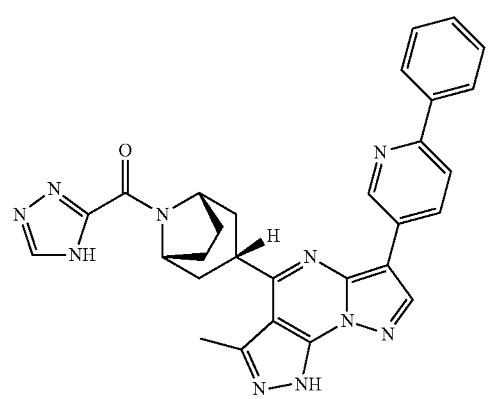 [SMILES: Cc1n[nH]c2c1c([C@@H]1C[C@H]3CC[C@@H](C1)N3C(=O)c1nnc[nH]1)nc1c(-c3ccc(-c4ccccc4)nc3)cnn12] | ((1R,3s,5S)-3-(3-methyl-6-(6-phenylpyridin-3-yl)-1H-dipyrazolo[1,5-a:4',3'-e]pyrimidin-4-yl)-8-azabicyclo[3.2.1]octan-8-yl)(4H-1,2,4-triazol-3-yl)methanone | 531.2/531.0 | A | B |

EXAMPLE 2

Preparation of ((1R,3s,5S)-3-(3-(6-phenylpyridin-3-yl)-8H-pyrazolo[1,5-a]pyrrolo[3,2-e]pyrimidin-5-yl)-8-azabicyclo[3.2.1]octan-8-yl)(4H-1,2,4-triazol-3-yl)methanone Step 1: Preparation of 5-((1R,3s,5S)-8-azabicyclo[3.2.1]octan-3-yl)-3-(6-phenylpyridin-3-yl)-8H-pyrazolo[1,5-a]pyrrolo[3,2-e]pyrimidine

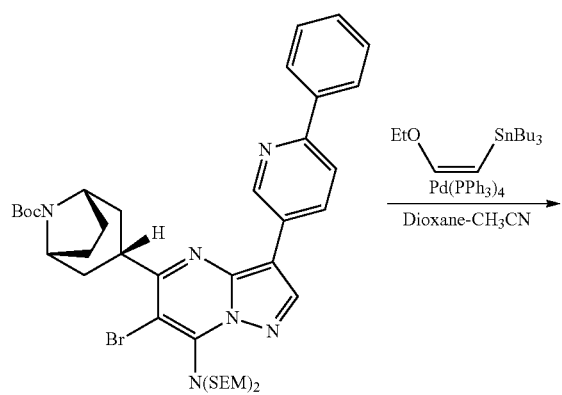

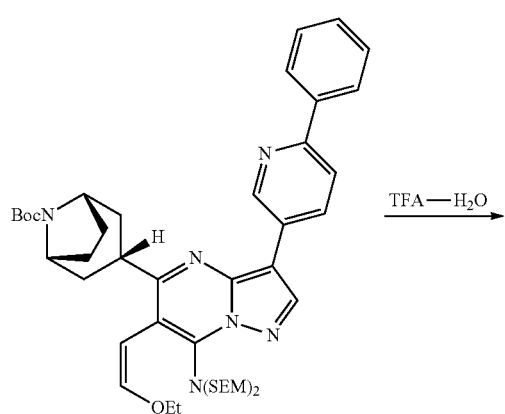

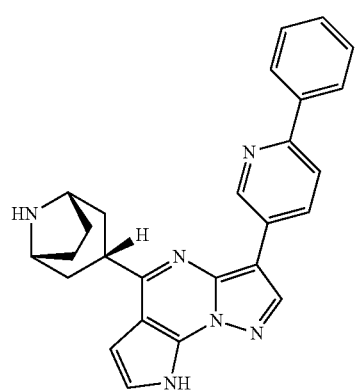

A mixture of (1R,3s,5S)-tert-butyl 3-(7-(bis((2-(trimethylsilyl)ethoxy)methyl)amino)-6-bromo-3-(6-phenylpyridin-3-yl)pyrazolo[1,5-a]pyrimidin-5-yl)-8-azabicyclo[3.2.1]octane-8-carboxylate (example 1, step 11, 160 mg, 0.19 mmol), Z-1-ethoxy-2(tributylstannyl)ethene (207.7 mg, 0.57 mmol), tetrakis(triphenylphosphine)palladium (22.2 mg, 0.019 66mmol) in dioxane (4 mL) and CH₃CN (0.7 mL) was degassed with argon for 1 minute and then heated at 125° C. in a sealed tube for 1 h under microwave condition. On cooling, the reaction mixture was filtered through 9:1 SiO₂: KF plug and concentrated in vacuo. The residue was then treated with 50% TFA/H₂O (10 mL) for 2 days. Concentration afforded crude 5-((1R,3s,5S)-8-azabicyclo[3.2.1]octan-3-yl)-3-(6-phenylpyridin-3-yl)-8H-pyrazolo[1,5-a]pyrrolo[3,2-e]pyrimidine which was used without purification.

Step 2: Preparation of ((1R,3s,5S)-3-(3-(6-phenylpyridin-3-yl)-8H-pyrazolo[1,5-a]pyrrolo[3,2-ue]pyrimidin-5-yl)-8-azabicyclo[3.2.1]octan-8-yl)(4H-1,2,4-triazol-3-yl)methanone

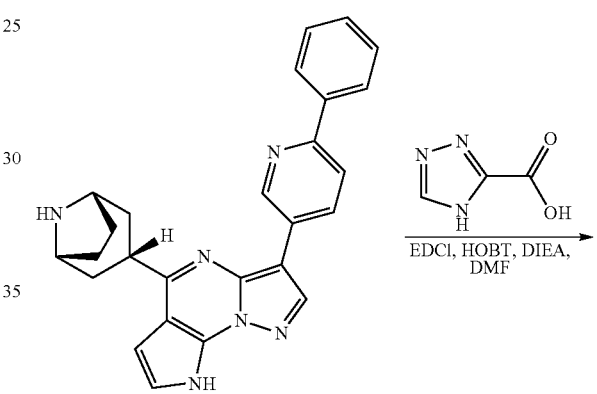

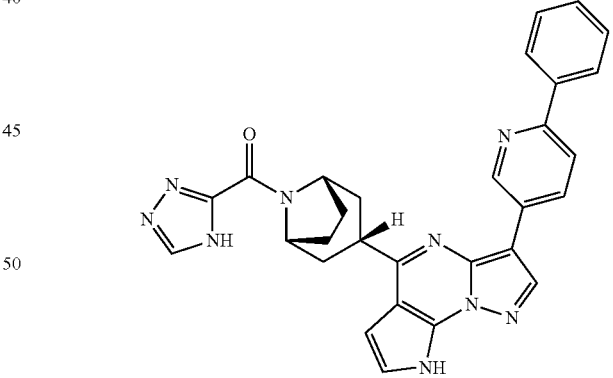

A mixture of 5-((1R,3s,5S)-8-azabicyclo[3.2.1]octan-3-yl)-3-(6-phenylpyridin-3-yl)-8H-pyrazolo[1,5-a]pyrrolo[3,2-e]pyrimidine (0.19 mmol), 1H-1,2,4-triazole-3-carboxylic acid (21.7 mg, 0.19 mmol), EDC (58.6 mg, 0.31 mmol), HOBt (25.9 mg, 0.19 mmol) and DIEA (200 uL, 1.15 mmol) in DMF (5 mL) was stirred at room temperature for 2 h. Purification with prep-LC provided ((1R,3s,5S)-3-(3-(6-phenylpyridin-3-yl)-8H-pyrazolo[1,5-a]pyrrolo[3,2-e]pyrimidin-5-yl)-8-azabicyclo[3.2.1]octan-8-yl)(4H-1,2,4-triazol-3-yl)methanone.

EXAMPLE 3

Preparation of ((1R,3s,5S)-3-(3-(6-(2-hydroxypropan-2-yl)pyridin-3-yl)-8H-pyrazolo[1,5-a]pyrrolo[3,2-e]pyrimidin-5-yl)-8-azabicyclo[3.2.1]octan-8-yl)(1H-1,2,4-triazol-3-yl)methanone Step 1: Preparation of 1-(5-(4,4,5,5-tetramethyl-1,3,2-dioxaborolan-2-yl)pyridin-2-yl)ethanone

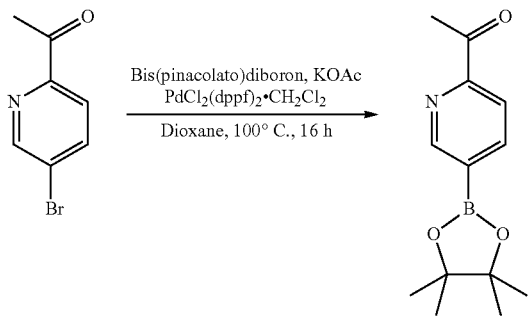

To 1-(5-bromopyridin-2-yl)ethanone (2 g, 10.1 mmol) in Dioxane (80 ml) was added bis(pinacolato)diboron (3.3 g, 13.1 mmol), PdCl$_2$(dppf)$_2$·CH$_2$Cl$_2$ (0.8 g, 1 mmol) and KOAc (3 g, 30.2 mmol). It was then degassed with Argon for five minute before heating at 100° C. for 16 hours, at which time LC/MS analysis confirmed full consumption of starting material. On cooling, the solvent was rotoevaporated, and the crude was redissolved in DCM (500 ml), washed with water (1×125 ml), brine (1×125 ml), and dried over MgSO$_4$. Solvent was removed in vacuo and the crude compound 1-(5-(4,4,5,5-tetramethyl-1,3,2-dioxaborolan-2-yl)pyridin-2-yl)ethanone was used for the next step without any further purification.

Step 2: Preparation of (1R,3s,5S)-tert-butyl 3-(3-(6-acetylpyridin-3-yl)-7-(bis((2-(trimethylsilyl)ethoxy)methyl)amino)pyrazolo[1,5-a]pyrimidin-5-yl)-8-azabicyclo[3.2.1]octane-8-carboxylate

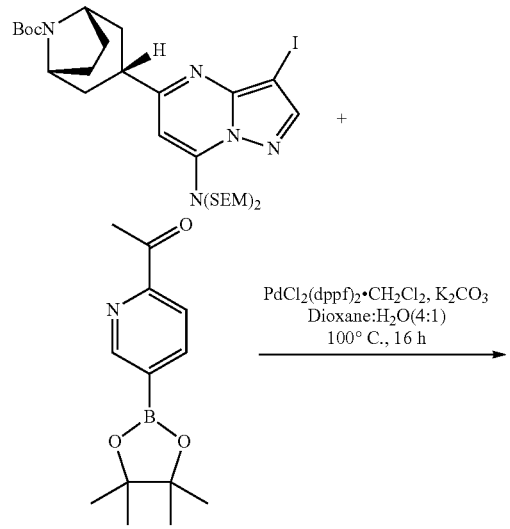

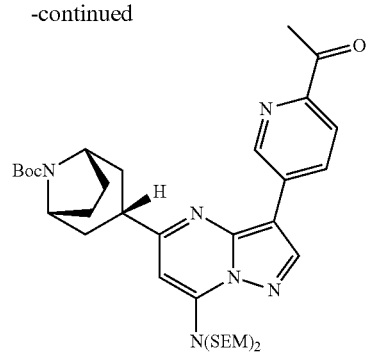

To crude 1-(5-(4,4,5,5-tetramethyl-1,3,2-dioxaborolan-2-yl)pyridin-2-yl)ethanone from step 2 in Dioxane (52 ml) and H$_2$O (13 ml) was added (1R,3s,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate 3 (4.9 g, 6.7 mmol), PdCl$_2$(dppf)$_2$·CH$_2$Cl$_2$ (0.5 g, 0.7 mmol) and K$_2$CO$_3$ (2.8 g, 20.1 mmol). The reaction was heated at 100° C. for 16 hours, at which time LC/MS analysis confirmed full consumption of starting material. On cooling, the solvent was rotoevaporated, and the crude was redissolved in DCM (500 ml), washed with water (1×125 ml), brine (1×125 ml), dried (MgSO$_4$) and concentrated in vacuo to crude. Gradient column chromatography on silica eluting with 0 to 50% EtOAc/hexanes gave the desired (1R,3s,5S)-tert-butyl 3-(3-(6-acetylpyridin-3-yl)-7-(bis((2-(trimethylsilyl)ethoxy)methyl)amino)pyrazolo[1,5-a]pyrimidin-5-yl)-8-azabicyclo[3.2.1]octane-8-carboxylate.

Step 3: Preparation of (1R,3s,5S)-tert-butyl 3-(7-(bis((2-(trimethylsilyl)ethoxy)methyl)amino)-3-(6-(2-hydroxypropan-2-yl)pyridin-3-yl)pyrazolo[1,5-a]pyrimidin-5-yl)-8-azabicyclo[3.2.1]octane-8-carboxylate

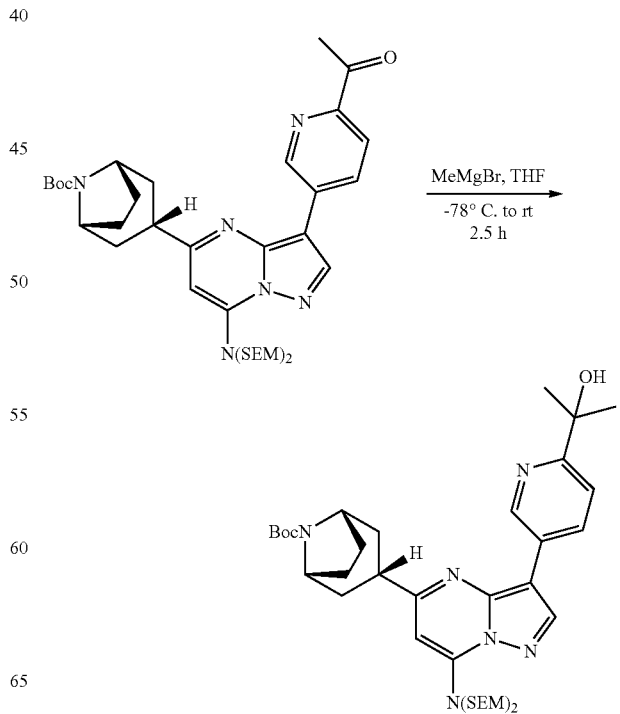

To a solution of (1R,3s,5S)-tert-butyl 3-(3-(6-acetylpyridin-3-yl)-7-(bis((2-(trimethylsilyl)ethoxy)methyl)amino)pyrazolo[1,5-a]pyrimidin-5-yl)-8-azabicyclo[3.2.1]octane-8-carboxylate (2.9 g, 4.1 mmol) in THF (75 ml) at −78° C. was added MeMgBr (1.4M in toluene/THF, 5.8 ml, 8.1 mmol) slowly. The reaction mixture was stirred at −78° C. for 10 min and the cooling bath was removed to warm it up to room temperature for 2.5 h. Saturated NH$_4$Cl solution (~10 mL) was added and stirring continued for 5 minutes before the reaction mixture was transferred to a separatory funnel using EtOAc (150 mL). Organics were then extracted with EtOAc (2×125 ml), and washed with water (2×30 ml), brine (1×30 ml), and dried over MgSO$_4$. Solvent was removed in vacuo and the residue was purified by column chromatography on silica gel. Elution with EtOAc/Hexanes (0-50%) gave desired product, (1R,3s,5S)-tert-butyl 3-(7-(bis((2-(trimethylsilyl)ethoxy)methyl)amino)-3-(6-(2-hydroxypropan-2-yl)pyridin-3-yl)pyrazolo[1,5-a]pyrimidin-5-yl)-8-azabicyclo[3.2.1]octane-8-carboxylate.

Step 4: Preparation of (1R,3s,5S)-tert-butyl 3-(7-(bis((2-(trimethylsilyl)ethoxy)methyl)amino)-6-bromo-3-(6-(2-hydroxypropan-2-yl)pyridin-3-yl)pyrazolo[1,5-a]pyrimidin-5-yl)-8-azabicyclo[3.2.1]octane-8-carboxylate

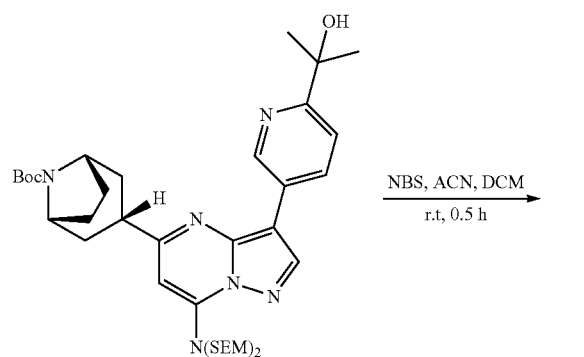

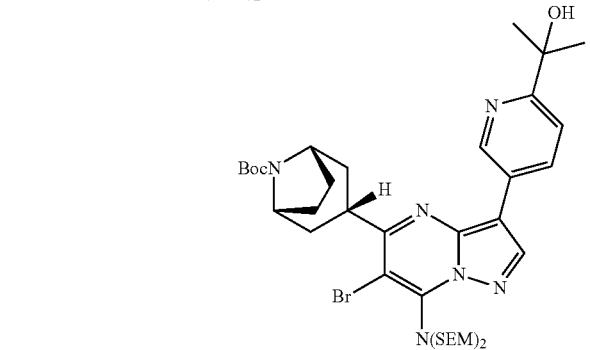

To (1R,3s,5S)-tert-butyl 3-(7-(bis((2-(trimethylsilyl)ethoxy)methyl)amino)-3-(6-(2-hydroxypropan-2-yl)pyridin-3-yl)pyrazolo[1,5-a]pyrimidin-5-yl)-8-azabicyclo[3.2.1]octane-8-carboxylate (1.5 g, 2 mmol) in CH$_3$CN (8 ml) and DCM (8 ml) was added N-bromosuccinimide (0.38 g, 2.2 mmol) portionwise and the resulting mixture was stirred at room temperature for 0.5 h, at which time LC/MS confirmed full conversion of starting material to product. Solvent was removed in vacuo and the residue was purified by column chromatography on silica gel. Elution with EtOAc/Hexanes (0-50%) gave desired product, (1R,3s,5S)-tert-butyl 3-(7-(bis((2-(trimethylsilyl)ethoxy)methyl)amino)-6-bromo-3-(6-(2-hydroxypropan-2-yl)pyridin-3-yl)pyrazolo[1,5-a]pyrimidin-5-yl)-8-azabicyclo[3.2.1]octane-8-carboxylate.

Step 5: Preparation of (1R,3s,5S)-tert-butyl 3-(7(bis((2-(trimethylsilyl)ethoxy)methyl)amino)-6-((E)-2-ethoxyvinyl)-3-(6-(2-hydroxypropan-2-yl)pyridin-3-yl)pyrazolo[1,5-a]pyrimidin-5-yl)-8-azabicyclo[3.2.1]octane-8-carboxylate

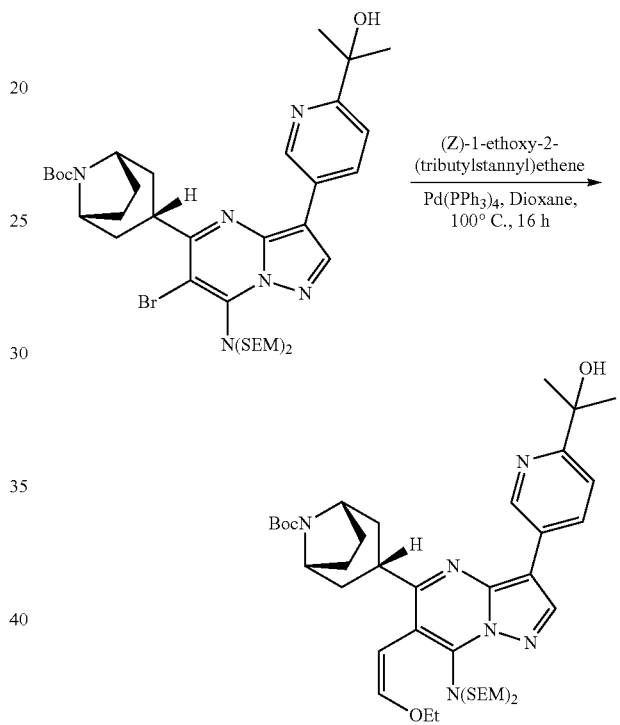

A mixture of compound (1R,3s,5S)-tert-butyl 3-(7-(bis((2-(trimethylsilyl)ethoxy)methyl)amino)-6-bromo-3-(6-(2-hydroxypropan-2-yl)pyridin-3-yl)pyrazolo[1,5-a]pyrimidin-5-yl)-8-azabicyclo[3.2.1]octane-8-carboxylate (0.7 g, 0.9 mmol), (Z)-1-ethoxy-2-(tributylstannyl)ethene (0.6 mL, 1.8 mmol), Tetrakis(triphenylphosphine)palladium (0.1 g, 0.1 mmol) in dioxane (7 mL) was degassed with argon for five minutes. It was then heated at 100° C. in a sealed tube for 16 hours, at which time LC/MS analysis confirmed full consumption of starting material. On cooling, the solvent was rotoevaporated, and the crude was redissolved in EtOAc (100 mL), washed with 0.5 M KF solution (1×10 mL), water (1×20 mL), brine (1×25 mL), and dried over MgSO$_4$. Solvent was removed in vacuo and the residue was purified by column chromatography on silica gel. Elution with EtOAc/Hexanes (0-80%) gave desired product, (1R,3s,5S)-tert-butyl 3-(7-(bis((2-(trimethylsilyl)ethoxy)methyl)amino)-6-((E)-2-ethoxyvinyl)-3-(6-(2-hydroxypropan-2-yl)pyridin-3-yl)pyrazolo[1,5-a]pyrimidin-5-yl)-8-azabicyclo[3.2.1]octane-8-carboxylate.

Step 6: Preparation of product 2-(5-(5-((1R,3s,5S)-8-azabicyclo[3.2.1]octan-3-yl)-8H-pyrazolo[1,5-a]pyrrolo[3,2-e]pyrimidin-3-yl)pyridin-2-yl)propan-2-ol

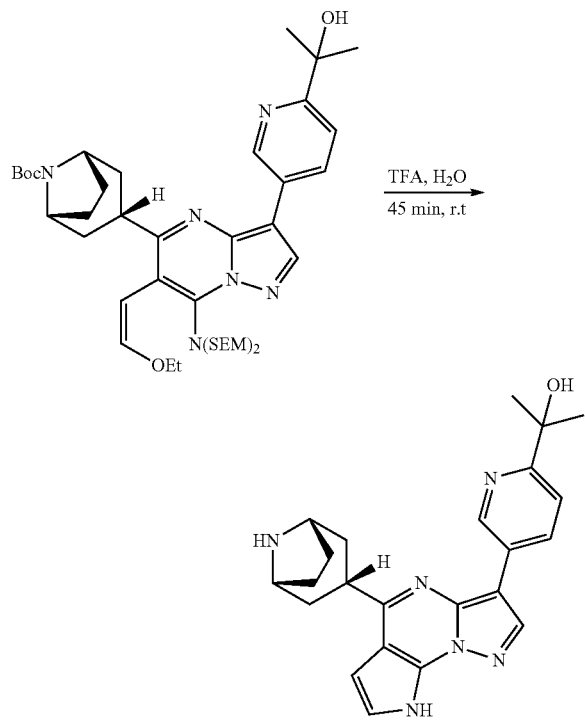

(1R,3s,5S)-tert-butyl 3-(7-(bis((2-(trimethylsilyl)ethoxy)methyl)amino)-6-((E)-2-ethoxyvinyl)-3-(6-(2-hydroxypropan-2-yl)pyridin-3-yl)pyrazolo[1,5-a]pyrimidin-5-yl)-8-azabicyclo[3.2.1]octane-8-carboxylate 12 (0.5 g, 0.6 mmol) was dissolved in a mixture of TFA (32 mL) and water (1.7 mL) at room temperature. Stirring continued for 4 hours at room temperature. LC/MS analysis confirmed full consumption of starting material to product. TFA along with water was rotoevaporated, and the crude product 2-(5-(5(1R,3s,5S)-8-azabicyclo[3.2.1]octan-3-yl)-8H-pyrazolo[1,5-a]pyrrolo[3,2-e]pyrimidin-3-yl)pyridin-2-yl)propan-2-ol was dried under the high vacuum for 24 hour, which was used without further purification for the next step.

Step 7: Preparation of compound ((1R,3s,5S)-3-(3-(6-(2-hydroxypropan-2-yl)pyridin-3-yl)-8H-pyrazolo[1,5-a]pyrrolo[3,2-e]pyrimidin-5-yl)-8-azabicyclo[3.2.1]octan-8-yl)(1H-1,2,4-triazol-3-yl)methanone

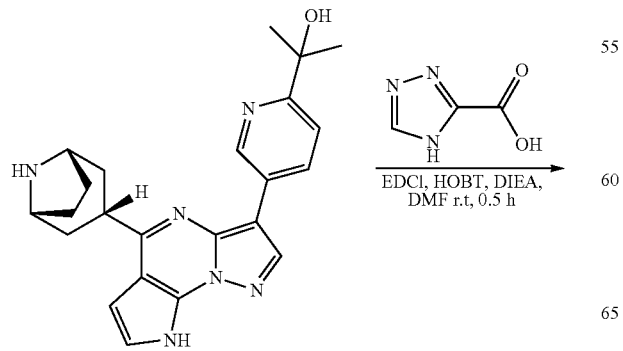

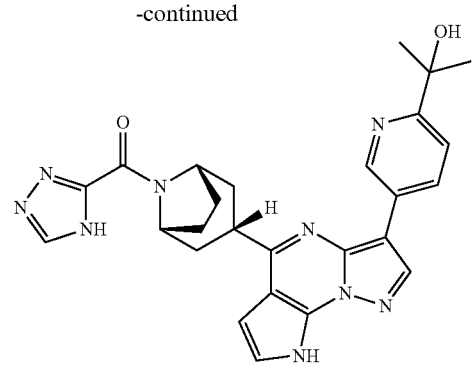

A mixture of 1H-1,2,4-triazole-3-carboxylic acid (22.6 mg, 0.2 mmol), EDCI (76.7 mg, 0.4 mmol), and 1-hydroxybenzotriazole (27 mg, 0.2 mmol) in DMF (2 mL) was stirred at room temperature for 10 min. Crude 2-(5-(5-((1R,3s,5S)-8-azabicyclo[3.2.1]octan-3-yl)-8H-pyrazolo[1,5-a]pyrrolo[3,2-e]pyrimidin-3-yl)pyridin-2-yl)propan-2-ol from step 6 (0.25 mmol) was added followed by N,N-diisopropylethylamine (0.18 mL, 1 mmol). It was stirred further for 20 minutes at room temperature at which time LC/MS analysis confirmed full consumption of starting material. Pure compound ((1R,3s,5S)-3-(3-(6-(2-hydroxypropan-2-yl)pyridin-3-yl)-8H-pyrazolo[1,5-a]pyrrolo[3,2-e]pyrimidin-5-yl)-8-azabicyclo[3.2.1]octan-8-yl)(1H-1,2,4-triazol-3-yl)methanone was isolated by preparative HPLC.

EXAMPLE 4

Preparation of 2-hydroxy-1-((1R,3s,5S)-3-(3-(6-(2-hydroxypropan-2-yl)pyridin-3-yl)-8H-pyrazolo[1,5-a]pyrrolo[3,2-e]pyrimidin-5-yl)-8-azabicyclo[3.2.1]octan-8-yl)ethanone

Step 1: Preparation of 2-hydroxy-1-((1R,3s,5S)-3-(3-(6-(2-hydroxypropan-2-yl)pyridin-3-yl)-8H-pyrazolo[1,5-a]pyrrolo[3,2-e]pyrimidin-5-yl)-8-azabicyclo[3.2.1]octan-8-yl)ethanone

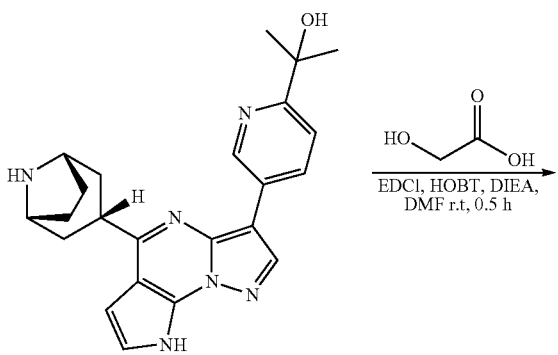

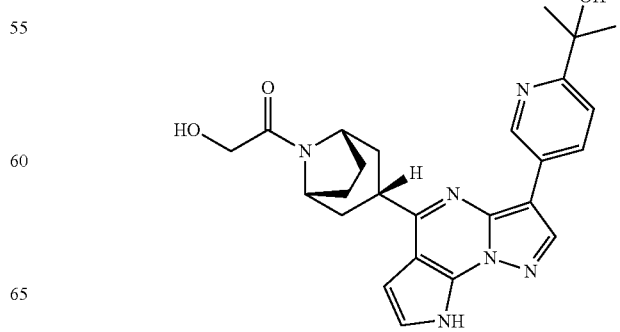

A mixture of glycolic acid (99.6 mg, 0.15 mmol), EDCI (57.5 mg, 0.3 mmol), and 1-hydroxybenzotriazole (22.3 mg, 0.15 mmol) in DMF (2 mL) was stirred at room temperature for 10 minutes. Compound 2-(5-(5-(((1R,3s,5S)-8-azabicyclo[3.2.1]octan-3-yl)-8H-pyrazolo[1,5-a]pyrrolo[3,2-e]pyrimidin-3-yl)pyridin-2-yl)propan-2-ol (example 3, step 6, 0.15 mmol) was added followed by N,N-diisopropylethylamine (0.13 mL, 0.75 mmol). It was stirred further for 20 minutes at room temperature at which time LC/MS analysis confirmed full consumption of starting material. Pure compound 2-hydroxy-1-((1R,3s,5S)-3-(3-(6-(2-hydroxypropan-2-yl)pyridin-3-yl)-8H-pyrazolo[1,5-a]pyrrolo[3,2-e]pyrimidin-5-yl)-8-azabicyclo[3.2.1]octan-8-yl)ethanone was isolated by preparative HPLC.

EXAMPLE 5

Preparation of 1-((1R,3s,5S)-3-(3-(6-(1H-imidazol-2-yl)pyridin-3-yl)-8H-pyrazolo[1,5-a]pyrrolo[3,2-e]pyrimidin-5-yl)-8-azabicyclo[3.2.1]octan-8-yl)-2-hydroxyethanone Step 1: Preparation of (1R,3s,5S)-tert-butyl 3-(7-(bis((2-(trimethylsilyl)ethoxy)methyl)amino)-3-(6-formylpyridin-3-yl)pyrazolo[1,5-a]pyrimidin-5-yl)-8-azabicyclo[3.2.1]octane-8-carboxylate

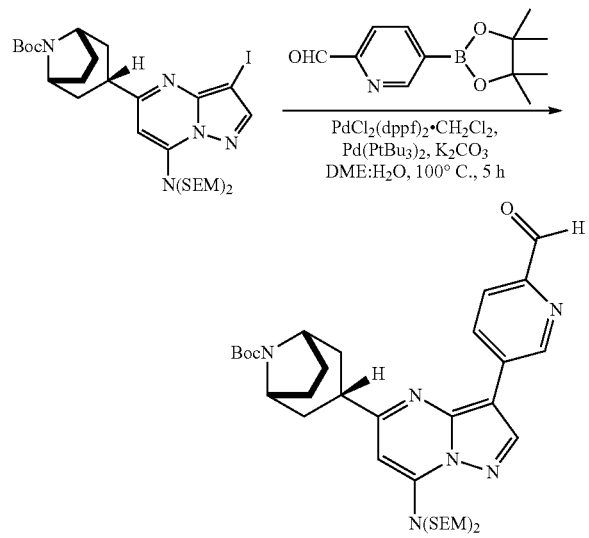

To a pressure tube were charged (1R,3s,5S)-tert-butyl 3-(7-(bis((2-(trimethylsilyl)ethoxy)methyl)amino)-3-iodopyrazolo[1,5-a]pyrimidin-5-yl)-8-azabicyclo[3.2.1]octane-8-carboxylate (9.4 g, 12.9 mmol), 2-formylpyridinyl-5-boronic acid pinacolo ester (6 g, 25.75 mmol), PdCl$_2$(dppf)$_2$ (2.1 g, 2.57 mmol), Pd(PtBu$_3$)$_2$ (80 mg, 0.16 mmol) and K$_2$CO$_3$ (5.3 g, 38.4 mmol), DME (80 mL) and water (40 mL). The mixture was degassed with Ar and stirred at 100° C. for 5 hours. On cooling, EtOAc (100 mL) was added, and resulting mixture was washed with water (1×60 mL), brine (1×125 mL), and dried over MgSO$_4$. After filtration and concentration the residue was purified on silica gel. Gradient elution with EtOAc/hexanes (0 to 40%) gave the desired product.

Step 2: Preparation of (1R,3s,5S)-tert-butyl 3-(7-(bis((2-(trimethylsilyl)ethoxy)methyl)amino)-6-bromo-3-(6-formylpyridin-3-yl)pyrazolo[1,5-a]pyrimidin-5-yl)-8-azabicyclo[3.2.1]octane-8-carboxylate

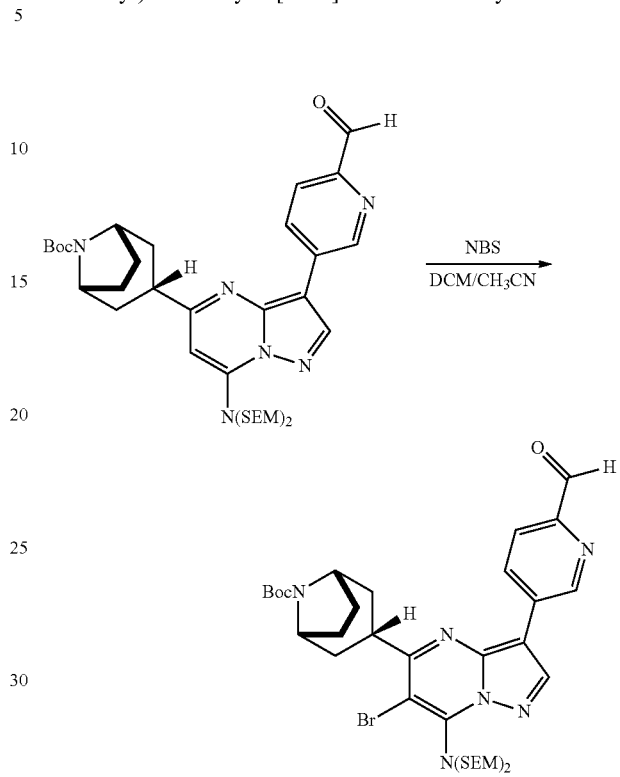

To a suspension of (1R,3s,5S)-tert-butyl 3-(7-(bis((2-(trimethylsilyl)ethoxy)methyl)amino)-3-(6-formylpyridin-3-yl)pyrazolo[1,5-a]pyrimidin-5-yl)-8-azabicyclo[3.2.1]octane-8-carboxylate (708 mg, 1 mmol) in DCM and acetonitrile (1:1, 4 mL) was added NBS (178 mg, 1 mmol) and the mixture was stirred for 5 minutes. After concentration, the residue was purified on silica gel. Gradient elution with EtOAc/hexanes (0 to 40%) gave the desired product.

Step 3: Preparation of (1R,3s,5S)-tert-butyl 3-(7-(bis((2-(trimethylsilyl)ethoxy)methyl)amino)-6-((Z)-2-ethoxyvinyl)-3-(6-formylpyridin-3-yl)pyrazolo[1,5-a]pyrimidin-5-yl)-8-azabicyclo[3.2.1]octane-8-carboxylate

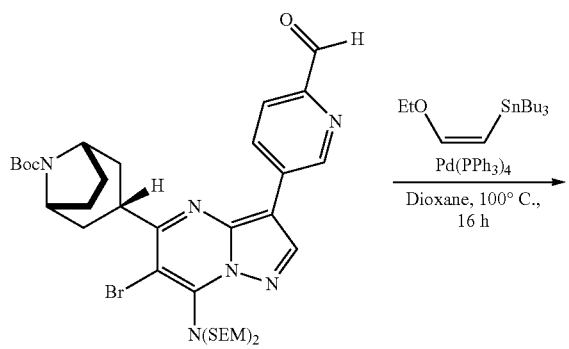

-continued

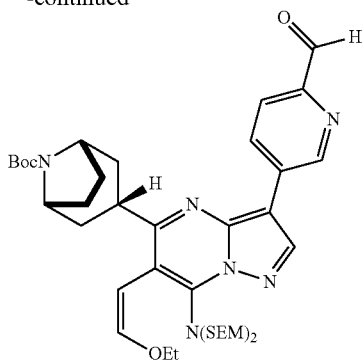

A mixture of compound (1R,3s,5S)-tert-butyl 3-(7-(bis((2-(trimethylsilyl)ethoxy)methyl)amino)-6-bromo-3-(6-formylpyridin-3-yl)pyrazolo[1,5-a]pyrimidin-5-yl)-8-azabicyclo[3.2.1]octane-8-carboxylate (583 mg, 0.74 mmol), Z-1-ethoxy-2(tributylstannyl)ethene (534 mg, 1.48 mmol), tetrakis(triphenylphosphine)palladium (80 mg, 0.069 mmol) in dioxane (4 mL) was degassed with argon for 1 minute. It was then heated at 100° C. in a sealed tube for 16 h. On cooling, the reaction mixture was diluted with EtOAc (30 mL), washed with 0.5 M KF solution (1×10 mL), brine (1×25 mL), and dried over MgSO₄. The solvent was removed in vacuo and the residue was purified by column chromatography on silica gel. Elution with EtOAc/Hexanes (0-30%) gave the title product as yellow oil.

Step 4: Preparation of (1R,3s,5S)-tert-butyl 3-(3-(6-(1H-imidazol-2-yl)pyridin-3-yl)-7-(bis((2-(trimethylsilyl)ethoxy)methyl)amino)-6-((Z)-2-ethoxyvinyl)pyrazolo[1,5-a]pyrimidin-5-yl)-8-azabicyclo[3.2.1]octane-8-carboxylate

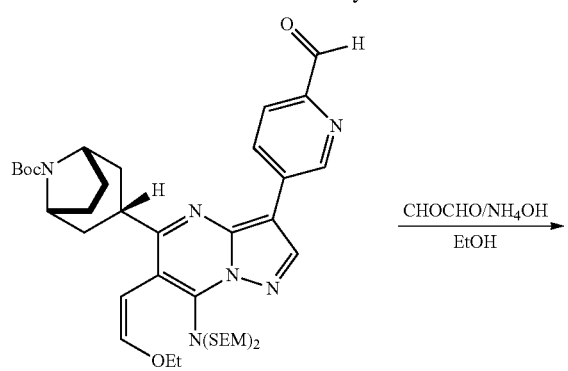

To a pressure tube were charged (1R,3s,5S)-tert-butyl 3-(7-(bis((2-(trimethylsilyl)ethoxy)methyl)amino)-6-((Z)-2-ethoxyvinyl)-3-(6-formylpyridin-3-yl)pyrazolo[1,5-a]pyrimidin-5-yl)-8-azabicyclo[3.2.1]octane-8-carboxylate (560 mg, 0.72 mmol) and EtOH (3 mL) and the solution was cooled to 0-5° C. by an ice bath. To the solution was added NH₄OH (28%, 0.8 mL), followed by glyoxal (40%, 163 µL). The tube was sealed and the reaction mixture was heated at 90° C. with stirring for 1 hour. After concentration under reduced pressure, the residue was re-taken into EtOAc (30 mL), washed with water (5 mL), brine (10 mL) and dried over MgSO₄. The solvent was removed in vacuo and the residue was purified by column chromatography on silica gel. Elution with EtOAc gave the title product.

Step 5: Preparation of 3-(6-(1H-imidazol-2-yl)pyridin-3-yl)-5-((1R,3s,5S)-8-azabicyclo[3.2.1]octan-3-yl)-8H-pyrazolo[1,5-a]pyrrolo[3,2-e]pyrimidine

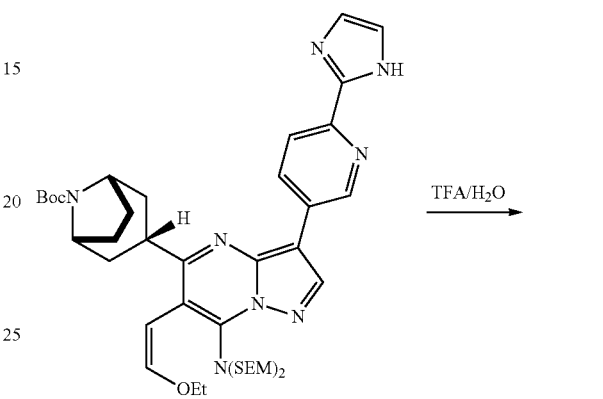

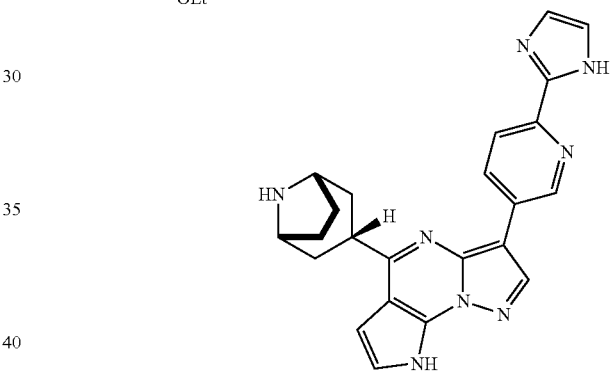

A mixture of (1R,3s,5S)-tert-butyl 3-(3-(6-(1H-imidazol-2-yl)pyridin-3-yl)-7-(bis((2-(trimethylsilyl)ethoxy)methyl)amino)-6-((Z)-2-ethoxyvinyl)pyrazolo[1,5-a]pyrimidin-5-yl)-8-azabicyclo[3.2.1]octane-8-carboxylate (420 mg) in TFA/water (1:1, 4 mL) was stirred at room temperature for 16 hours, concentrated and lyophilized to provide the title compound as TFA salt.

Step 6: Preparation of 1-((1R,3s,5S)-3-(3-(6-(1H-imidazol-2-yl)pyridin-3-yl)-6-acetyl-7-aminopyrazolo[1,5-a]pyrimidin-5-yl)-8-azabicyclo[3.2.1]octan-8-yl)-2-hydroxyethanone

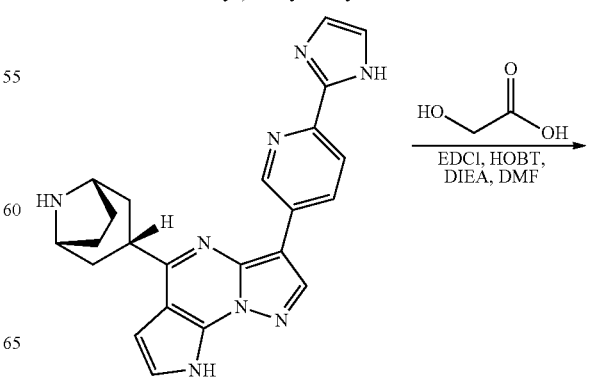

-continued

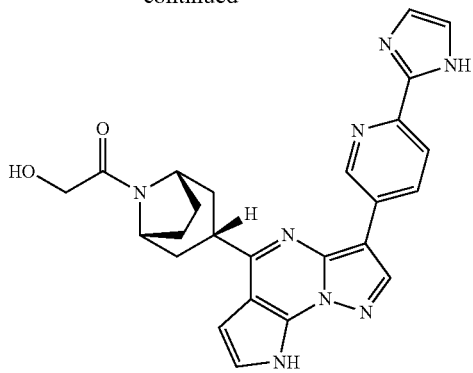

A mixture of glycolic acid (25 mg, 0.3 mmol), EDCI (58 mg, 0.3 mmol), and 1-hydroxybenzotriazole (27 mg, 0.2 mmol) in DMF (1 ml) was warmed up to a homogeneous solution. This mixture was added into a solution of 3-(6-(1H-imidazol-2-yl)pyridin-3-yl)-5-((1R,3s,5S)-8-azabicyclo[3.2.1]octan-3-yl)-8H -pyrazolo[1,5-a]pyrrolo[3,2-e]pyrimidine (0.2 mmol) and N,N-diisopropylethylamine (104 uL, 0.6 mmol) in DMF (2 mL). It was stirred further for 10 min and the crude compound was directly purified by HPLC to afford the desired product.

EXAMPLE 6

Preparation of ((1R,3s,5S)-3-(3-(6-(1H-imidazol-2-yl)pyridin-3-yl)-8H-pyrazolo[1,5-a]pyrrolo[3,2-e]pyrimidin-5-yl)-8-azabicyclo[3.2.1]octan-8-yl)(4H-1,2,4-triazol-3-yl)methanone By applying the chemistry described in Example 5, steps 6, and using suitable starting materials, of ((1R,3s,5S)-3-(3-(6-(1H-imidazol-2-yl)pyridin-3-yl)-8H-pyrazolo[1,5-a]pyrrolo[3,2-e]pyrimidin-5-yl)-8-azabicyclo[3.2.1]octan-8-yl)(4H-1,2,4-triazol-3-yl)methanone was synthesized.

| # | Structures | Compound Name | M + H (calculated)/ M + H (observed) | pAKT S473 IC50 | p4E-BP1 Thr37/46 IC50 |
|---|---|---|---|---|---|
| 2 | 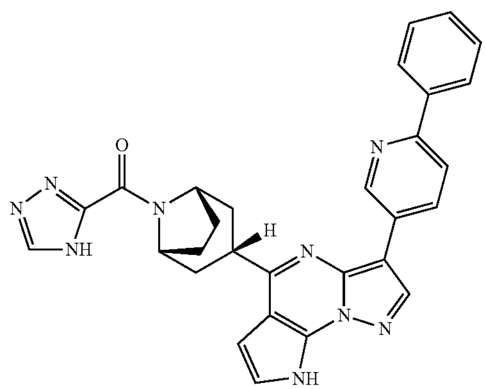 [SMILES: O=C(c1nnc[nH]1)N1[C@@H]2CC[C@H]1C[C@H](c1nc3c(-c4ccc(-c5ccccc5)nc4)cnn3c3[nH]ccc13)C2] | ((1R,3s,5S)-3-(3-(6-phenylpyridin-3-yl)-8H-pyrazolo[1,5-a]pyrrolo[3,2-e]pyrimidin-5-yl)-8-azabicyclo[3.2.1]octan-8-yl)(4H-1,2,4-triazol-3-yl)methanone | 516.2/516.3 | A | A |
| 3 | 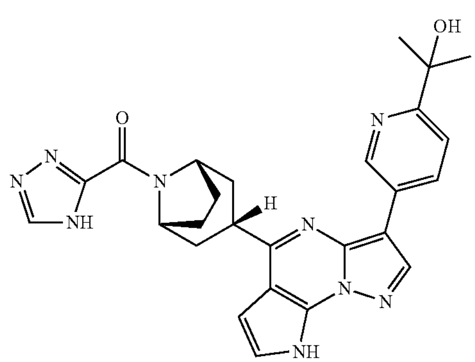 [SMILES: CC(C)(O)c1ccc(-c2cnn3c2nc([C@@H]2C[C@H]4CC[C@@H](C2)N4C(=O)c2nnc[nH]2)c2cc[nH]c23)cn1] | ((1R,3s,5S)-3-(3-(6-(2-hydroxypropan-2-yl)pyridin-3-yl)-8H-pyrazolo[1,5-a]pyrrolo[3,2-e]pyrimidin-5-yl)-8-azabicyclo[3.2.1]octan-8-yl)(1H-1,2,4-triazol-3-yl)methanone | 498.2/498.0 | B | B |

-continued

| # | Structures | Compound Name | M + H (calculated)/ M + H (observed) | pAKT S473 IC50 | p4E-BP1 Thr37/46 IC50 |
|---|---|---|---|---|---|
| 4 | 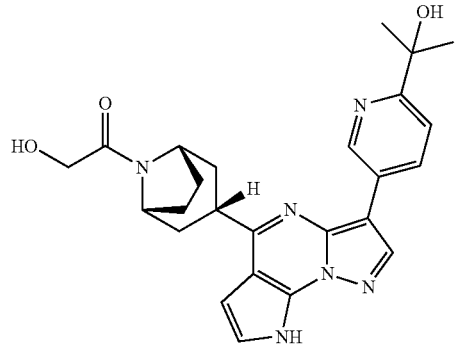 [SMILES: CC(C)(O)c1ccc(-c2cnn3c2nc([C@@H]2C[C@H]4CC[C@@H](C2)N4C(=O)CO)c2cc[nH]c23)cn1] | 2-hydroxy-1-((1R,3s,5S)-3-(3-(6-(2-hydroxypropan-2-yl)pyridin-3-yl)-8H-pyrazolo[1,5-a]pyrrolo[3,2-e]pyrimidin-5-yl)-8-azabicyclo[3.2.1]octan-8-yl)ethanone | 461.2/461.0 | C | B |
| 5 | 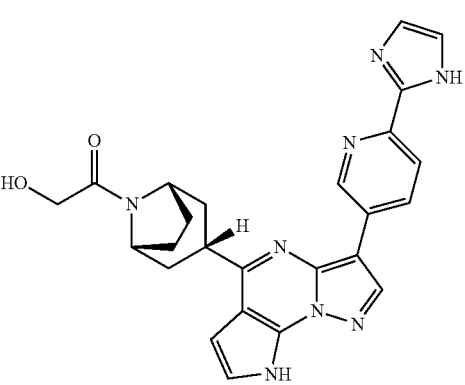 [SMILES: O=C(CO)N1[C@@H]2CC[C@H]1C[C@H](c1nc3c(-c4ccc(-c5ncc[nH]5)nc4)cnn3c3[nH]ccc13)C2] | 1-((1R,3s,5S)-3-(3-(6-(1H-imidazol-2-yl)pyridin-3-yl)-8H-pyrazolo[1,5-a]pyrrolo[3,2-e]pyrimidin-5-yl)-8-azabicyclo[3.2.1]octan-8-yl)-2-hydroxyethanone | 469.2/469.0 | A | B |
| 6 | 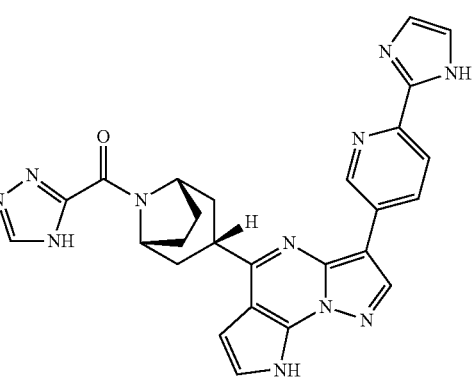 | ((1R,3s,5S)-3-(3-(6-(1H-imidazol-2-yl)pyridin-3-yl)-8H-pyrazolo[1,5-a]pyrrolo[3,2-e]pyrimidin-5-yl)-8-azabicyclo[3.2.1]octan-8-yl)(4H-1,2,4-triazol-3-yl)methanone | 506.2/505.9 | A | A |

EXAMPLE 7 mTOR Kinase Assay

Methods: An HTRF mTOR enzyme assay was developed to assess the compounds' inhibitory activity. The mTOR assay buffer contained 10 mM Hepes (pH 7.4), 50 mM NaCl, 100 μg/ml BSA, 50 mM μ-glycerophosphate, 10 mM MnCl$_2$ and 0.5 mM DTT. An active truncated mTOR enzyme was prepared similarly to that reported by Toral-Barza et al., Biochemical and Biophysical Research Communications 332, pp 304-310 (2005). 20 ng of human mTOR enzyme (<5% pure was preincubated with the compound for 10 minutes followed by the addition of 5 μM ATP and 0.2 μM GST-S6K (Zhang et al., Protein Expression and Purification 46, pp 414-420 (2006)). The reaction was incubated for one hour at 30° C. Anti phospho p70-S6K (Thr389) (~1.7 ng/well, anti -phospho-p70S6K-cryptate (Pho-p70S6-Kin-K cat#64CUSKAY, from Cisbio)) and anti GST-XL665 (1:1 Ratio with the substrate GST-S6K, anti GST-XL665, cat#61GSTXLB) Cisbio) were added after the reaction was stopped. The plates were read (PHERAstar, BMG) at least 2 hours after adding the anti phospho p70-S6K and the anti GST-XL665.

IC$_{50}$ DETERMINATIONS: Dose-response curves were plotted from the inhibition data generated, each in duplicate, from 8 point serial dilutions of inhibitory compounds. Concentration of compound was plotted against the HTRF em665/em590 ratio signal. To generate IC$_{50}$ values, the dose-response curves were fitted to a standard sigmoidal curve and $IC_{50}$ values were derived by nonlinear regression analysis.

EXAMPLE 8 mTOR Target Engagement Assay

The target engagement of mTOR kinase inhibitors was evaluated using an immunofluorescent cell-based assay. In this assay, inhibition of mTORC1 activity was measured by the reduction in the level of phosphorylated 4E-BP1Thr37/46 (p4E-BP1 Thr37/46), and inhibition of mTORC2 activity was measured by the reduction of phosphorylated AKTSer473 (pAKT S473).

PC3 cells (prostate tumor cell-line that contains a mutation in the tumor suppressor PTEN, that promotes the phosphorylation and activation of AKT and 4E-BP 1) were used in the immunofluorescence assay. PC3 cells were seeded on 384 well plates (black clear bottom, Matrix #4332) overnight. PC3 cells were then treated with 40 µl of the serially diluted test compounds (in 5% fetal bovine serum, F12 medium containing 0.25% DMSO) for ninety minutes at 37° C. The test compound solution was removed, and the plates were washed gently two times with 25 µl phosphate buffered saline (PBS). The cells were fixed by adding 25 µl of Prefer reagent (from Anatech LTD, Cat#414, a glyoxal fixative for fixing proteins within a cell) for sixty minutes followed by three washes with PBS. 5% Goat serum in PBS/0.3% Triton was used to block non-specific binding (60 minutes).

The primary antibodies targeting pAKT S473 and p4E-BP1 Thr37/46 were diluted into PBS/0.3% Triton and incubated with the cells overnight at 4° C. The antibodies targeting pAKTS473 (Cat#4085, Cell signaling) and p4E-BP1 Thr37/46 (Cat#2855, Cell signaling) were used at a 1:100 dilution. Plates were washed three times with PBS/0.1% Tween 20 before adding the secondary antibody at a 1:200 dilution. (goat anti-rabbit containing a fluorescent label, Alexa Fluor 488, Cat# A11008, Invitrogen) in PBS/0.3% Triton for 60 minutes.

Finally, the plates were washed three times with PBS/0.1% Tween 20 and the fluorescent intensity was read using an Analyst HT from Molecular Devices. The fluorescent intensity values from the serially diluted compound treatment group were analyzed using the Xlfit 4 program (Microsoft) (Formula 205: Y=Bottom+(Top-Bottom)/(1+($IC_{50}$/X)^Hillslope) to generate the $IC_{50}$ value. Where Top is the maximum signal without Compound (+DMSO only) and Bottom represents maximum inhibition. Y is the fluorescence at some compound concentration. The control used to determine the fluorescent intensities for 100% pAKT S473 or 100% phosphorylated p4E-BP1 Thr37/46 were measured from untreated wells that contained only DMSO, instead of test compound.

The above tables list representative compounds of the invention with activity data whereby the IC50 values are rated "A", "B," "C," or "D." The IC50 values are rated "A" for $IC_{50}$ values in the range of 1 nM to 100 nM, "B" for $IC_{50}$ values in the range from 100 nM to 1000 nM, "C" for $IC_{50}$ values in the range from 1000 nM to 2000 nM, "D" for $IC_{50}$ values in the range from 2000 nM to 5000 nM and "E" for $IC_{50}$ values of 5000 nM to 15 µM.

While this invention has been particularly shown and described with references to embodiments thereof, it will be understood by those skilled in the art that various changes in form and details may be made therein without departing from the meaning of the invention described. Rather, the scope of the invention is defined by the claims that follow.

What is claimed is:
1. A compound of Formula I

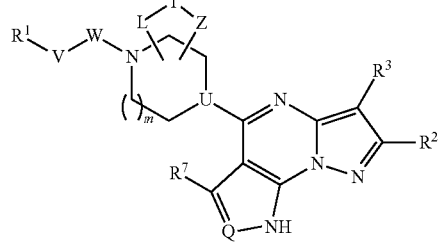

U is N or CH;
W is absent, or W is selected from the group consisting of C(O), S(O), S(O)$_2$, $C_1$-$C_4$ alkylene, $C_3$-$C_8$ cycloalkyl, phenyl, 5- to 6-membered heteroaryl, and 3- to 8-membered heterocyclyl;
V is absent, or V is selected from the group consisting of C(O), O, S, N(H), N($C_1$-$C_3$ alkyl), N($C_3$-$C_8$ cycloalkyl), S(O), S(O)$_2$, and $C_1$-$C_4$ alkylene;
or W and V together form a $C_3$-$C_8$ cycloalkyl, phenyl, 5- to 6-membered heteroaryl, or 3 to 8-membered heterocyclyl ring;
$R^1$ is selected from the group consisting of
(i) $C_1$-$C_6$ alkyl or $C_3$-$C_{10}$ cycloalkyl, wherein said alkyl or cycloalkyl of $R^1$ is unsubstituted or substituted with one to three moieties independently selected from the group consisting of hydroxy, $C_1$-$C_6$ alkoxy, halo, trifluoromethyl, carboxy, 5- to 6-membered heteroaryl, —SO$_2$H, $C_1$-$C_6$ alkyl-C(O)—NH—, $C_1$-$C_6$ alkyl-SO$_2$—NH—, and $C_1$-$C_6$ alkyl-SO—NH—;
(ii) 3- to 8-membered heterocyclyl wherein said heterocyclyl of $R^1$ is unsubstituted or substituted with one to three moieties independently selected from the group consisting of halo, $C_1$-$C_6$ alkyl, $C_1$-$C_6$ alkoxy, cyano, hydroxy, amino, $C_1$-$C_6$ alkylamino, and $C_1$-$C_6$ dialkylamino;
(iii) $C_6$-$C_{10}$ aryl or 5- to 10-membered heteroaryl, wherein said aryl or heteroaryl of $R^1$ is unsubstituted or is substituted with one to three moieties independently selected from the group consisting of halo, trifluoromethyl, trifluoromethoxy, $C_1$-$C_6$ alkyl, $C_1$-$C_6$ alkoxy, cyano, hydroxy, amino, $C_1$-$C_6$ alkylamino, and $C_1$-$C_6$ dialkylamino; and
(iv) —N(H)OH or —N(H)—$C_1$-$C_3$ alkoxy;
L and Z are bonded to any two carbons of the ring and are independently selected from the group consisting of CH$_2$, C(H)($R^{10}$), C($R^{10}$)($R^{11}$), N($R^{10}$), C(O), O, S, S(O) and S(O)$_2$;
T is not present such that L is bonded directly to Z, or T is selected from the group consisting of CH$_2$, C(H)($R^{10}$), C($R^{10}$)($R^{11}$), N($R^{10}$), C(O), O, S, S(O) and S(O)$_2$ and $C_1$-$C_4$ alkylene, wherein said alkylene of T is unsubstituted or substituted with 1 to two substituents selected from the group consisting of $C_1$-$C_3$ alkyl, halo, hydroxyl, $C_1$-$C_3$ alkoxy, amino, $C_1$-$C_3$ alkylamino and $C_1$-$C_3$ dialkylamino;
$R^a$ and $R^b$ are independently selected from H, halogen and $C_1$-$C_6$ alkyl;
$R^2$ is selected from the group consisting of H, halogen, $C_1$-$C_6$alkyl, $C_2$-$C_6$alkenyl, $C_2$-$C_6$alkynyl, $C_1$-$C_6$haloalkyl, $C_3$-$C_8$cycloalkyl, —CN, —NR$^8$R$^9$, —OR$^9$, SR$^9$, —S(O)R$^9$, —S(O$_2$)R$^9$, $C_6$-$C_{10}$aryl, 5- to 10-membered heteroaryl, 5- to 10-membered heterocyclenyl, 5- to 10-membered heterocyclyl, $C_3$-$C_8$cycloalkyl$C_1$-$C_6$alkyl, $C_6$-$C_{10}$aryl$C_1$-$C_6$alkyl, 5- to 10-membered heteroaryl$C_1$-$C_6$alkyl, 5- to 10-membered heterocyclyl$C_1$-$C_6$alkyl, 5- to 10-membered heterocyclenyl$C_1$-$C_6$alkyl;

$R^3$ is selected from the group consisting of H, halogen, $C_1$-$C_6$ alkyl, $C_2$-$C_6$ alkenyl, $C_2$-$C_6$ alkynyl, halo-$C_1$-$C_6$alkyl, —$CF_3$, —$C(O)R^9$, $C_6$-$C_{10}$aryl, $C_3$-$C_8$cycloalkyl, 5- to 10-membered heteroaryl, 5- to 10-membered heterocyclyl, 5- to 10-membered heterocyclenyl, $C_6$-$C_{10}$aryl$C_1$-$C_6$alkyl, $C_3$-$C_8$cycloalkyl$C_1$-$C_6$alkyl, 5- to 10-membered heteroaryl$C_1$-$C_6$alkyl, 5- to 10-membered heterocyclyl$C_1$-$C_6$alkyl and 5- to 10-membered heterocyclenyl$C_1$-$C_6$alkyl, wherein each of said aryl, cycloalkyl, heteroaryl, heterocyclyl, heterocyclenyl, arylalkyl, cycloalkylalkyl, heteroarylalkyl, heterocyclylalkyl and heterocyclenylalkyl is unsubstituted or substituted with one to three moieties which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, —$(CR^aR^b)_nOR^9$, —$(CR^aR^b)_nOR^9$, —$(CR^aR^b)_nNR^8R^9$, —$(CR^aR^b)_nNR^8$, —$NR^8R^9$, —$(CR^aR^b)_nC(O)R^9$, —$(CR^aR^b)_nC(O)O$—$C_1$-$C_6$alkyl, —O-halo$C_1$-$C_6$alkyl, —$(CR^aR^b)_nC(O)NR^8R^9$, —$(CR^aR^b)_nC(O)NR^8S(O)_2R^9$, —$(CR^aR^b)_nNR^8C(O)R^9$, —$(CR^aR^b)_nNR^8C(O)OR^9$, —$(CR^aR^b)_nNR^8C(O)NR^8R^9$, —$(CR^aR^b)_nS(O)_2NR^8R^9$, —$(CR^aR^b)_nS(O)_2NR^8C(O)R^9$, —$(CR^aR^b)_nNR^8S(O)_2R^9$, —$(CR^aR^b)_nSR^9$, —$(CR^aR^b)_nS(O)_2R^9$, $C_6$-$C_{10}$aryl, 5- to 10-membered heteroaryl, 5- to 10-membered heterocyclenyl, 5- to 10-membered heterocyclyl, $C_6$-$C_{10}$arylalkyl, 5- to 10-membered heteroarylalkyl, 5- to 10-membered heterocyclenylalkyl and 5- to 10-membered heterocyclylalkyl wherein each of said alkyl, cycloalkyl, aryl, heteroaryl, heterocyclyl, heterocyclenyl, arylalkyl, cycloalkylalkyl, heteroarylalkyl, heterocyclylalkyl and heterocyclenylalkyl is unsubstituted or substituted with one to five moieties, which can be the same or different, each moiety being selected from the group consisting of halogen, $C_1$-$C_6$alkyl, $C_3$-$C_8$cycloalkyl, —$CF_3$, —CN, —C(O)OH, —$(CR^aR^b)_nC(O)OH$, —$OCF_3$, —O-halo$C_1$-$C_6$alkyl, —$OR^9$, —$C(O)R^9$, —$NR^8R^9$, —$C(O)O$—$C_1$-$C_6$alkyl, —$C(O)NR^8R^9$, —$NR^8C(O)R^9$, —$S(O)_2NR^8R^9$, —$NR^8S(O)_2R^9$, —$SR^9$, and —$S(O)_2R^9$;

$R^6$ and $R^7$ are independently selected from the group consisting of H, halogen, $C_1$-$C_6$alkyl, $C_3$-$C_8$cycloalkyl, —$CF_3$, —CN, —$(CR^aR^b)_nC(O)OH$, —$OCF_3$, —$OR^9$, —$C(O)R^9$, —$NR^8R^9$, —$C(O)O$—$C_1$-$C_6$alkyl, —$CR^aR^b$, —$OR^a$, —$S(O)R^a$, —$C(O)OR^a$, —$S(O)_2NR^aR^b$, —$NR^aC(O)R^b$, —$NR^aS(O)_2R^b$, —$C(O)NR^8R^9$, —$SR^9$, and —$S(O)_2R^9$;

$R^8$ and $R^9$ are independently selected from the group consisting of H, OH, $C_1$—$C_6$alkyl, $C_3$-$C_8$cycloalkyl, $C_6$-$C_{10}$aryl, 5- to 10-membered heteroaryl, 5- to 10-membered heterocyclenyl, 5- to 10-membered heterocyclyl, $C_3$-$C_8$cycloalkyl$C_1$-$C_6$alkyl, $C_6$-$C_{10}$aryl$C_1$-$C_6$alkyl, 5- to 10-membered heteroaryl$C_1$-$C_6$alkyl, 5- to 10-membered heterocyclyl$C_1$-$C_6$alkyl, 5- to 10-membered heterocyclenyl$C_1$-$C_6$alkyl, and said alkyl, cycloalkyl, aryl, heteroaryl, heterocyclenyl, heterocyclyl, cycloalkylalkyl, arylalkyl, heteroarylalkyl, heterocyclenylalkyl or heterocyclylalkyl is optionally substituted with halogen, $C_1$-$C_6$alkyl, $C_3$-$C_8$cycloalkyl, —$CF_3$, —CN, —$(CR^aR^b)_nC(O)OH$, —$OCF_3$, —$OR^a$, —C(O), amino, —C(O)O—$C_1$-$C_6$alkyl, —C(O)$NR^aR^b$, —$SR^a$, and —$S(O_2)R^a$; or $R^8$ and $R^9$ together with the nitrogen atom to which they are attached form a 3- to 6-membered heterocyclyl ring;

$R^{10}$ and $R^{11}$ are independently selected from the group consisting of H, $C_1$-$C_3$alkyl, halo, hydroxyl, $C_1$-$C_3$alkoxy, amino, $C_1$-$C_3$alkylamino and $C_1$-$C_3$dialkylamino;

Q is N or $CR^6$;

n is independently 0, 1, 2, 3 or 4;

m is independently 0, 1, 2, 3 or 4;

or a pharmaceutically acceptable salt thereof.

2. The compound of claim 1, wherein

L and Z are both $CH_2$, and T is not present.

$R^a$ and $R^b$ are independently selected from H and $C_1$-$C_6$ alkyl;

$R^2$ is H;

$R^3$ is selected from the group consisting of $C_6$-$C_{10}$aryl, 5- to 10-membered heteroaryl, wherein each of said aryl or heteroaryl is unsubstituted or substituted with one to three moieties which can be the same or different, each moiety being selected from the group consisting of halogen, $C_1$-$C_6$alkyl, $C_6$-$C_{10}$aryl, 5- to 10-membered heteroaryl, —$CF_3$, —CN, —C(O)OH, —$(CR^aR^b)_nC(O)OH$, —$OCF_3$, —O-halo$C_1$-$C_6$alkyl, —$OR^8$, —$C(O)R^8$, —$NR^8R^9$, —C(O)O—$C_1$-$C_6$alkyl, —$C(O)NR^8R^9$, —$NR^8C(O)R^9$, —$S(O)_2NR^8R^9$, —$NR^8S(O)_2R^9$, —$SR^8$, and —$S(O)_2R^8$, wherein each of said heteroaryl or aryl is unsubstituted or substituted with one to three moieties, which can be the same or different, each moiety being selected from the group consisting of halogen, $C_1$-$C_6$alkyl, —$CF_3$, —CN, —C(O)OH, —$(CR^aR^b)_nC(O)OH$, —$OCF_3$, —O-halo$C_1$-$C_6$alkyl, —$OR^a$, —$C(O)R^a$, —$NR^aR^b$, —C(O)O—$C_1$-$C_6$alkyl, —$C(O)NR^aR^b$, —$NR^aC(O)R^b$, —$S(O)_2NR^aR^b$, —$NR^aS(O)_2R^b$, —$SR^a$, and —$S(O)_2R^a$;

$R^6$ and $R^7$ are independently selected from the group consisting of H, —$OR^a$, —$NR^aR^b$, —$SR^a$, —$S(O)R^a$, —$S(O)_2R^a$, —$C(O)C_1$-$C_6$alkyl, —$C(O)NR^aR^b$, —$C(O)OR^a$, —$S(O)_2NR^aR^b$, —$NR^aC(O)R^b$, —$NR^aS(O_2)R^b$, $C_1$-$C_6$alkyl, $C_1$-$C_6$alkoxy, halogen, hydroxyl, amino and —CN;

$R^8$ and $R^9$ are independently selected from the group consisting of H, OH, $C_1$—$C_6$alkyl, $C_3$-$C_8$cycloalkyl, $C_6$-$C_{10}$aryl, 5- to 10-membered heteroaryl, 5- to 10-membered heterocyclenyl, 5- to 10-membered heterocyclyl, $C_3$-$C_8$cycloalkyl$C_1$-$C_6$alkyl, $C_6$-$C_{10}$aryl$C_1$-$C_6$alkyl, 5- to 10-membered heteroaryl$C_1$-$C_6$alkyl, 5- to 10-membered heterocyclyl$C_1$-$C_6$alkyl, 5- to 10-membered heterocyclenyl$C_1$-$C_6$alkyl, and said alkyl, cycloalkyl, aryl, heteroaryl, heterocyclenyl, heterocyclyl, cycloalkylalkyl, arylalkyl, heteroarylalkyl, heterocyclenylalkyl or heterocyclylalkyl is optionally substituted with halogen, $C_1$-$C_6$alkyl, $C_3$-$C_8$cycloalkyl, —$CF_3$, —CN, —$(CR^aR^b)_nC(O)OH$, —$OCF_3$, —$OR^a$, —C(O), amino, —C(O)O—$C_1$-$C_6$alkyl, —C(O)$NR^aR^b$, —$SR^a$, and —$S(O_2)R^a$;

Q is CR6;

n is independently 0, 1 or 2;

m is 1;

or a pharmaceutically acceptable salt thereof.

3. The compound of claim 1, wherein W is C(O).

4. The compound of claims 1, wherein V is absent.

5. The compound of claims 1, wherein $R^1$ is selected from the group consisting of (i) $C_1$-$C_6$ alkyl or $C_3$-$C_{10}$ cycloalkyl, wherein said alkyl or cycloalkyl of $R^1$ is unsubstituted or substituted with one to three moieties independently selected from the group consisting of hydroxy, $C_1$-$C_6$ alkoxy, fluoro, trifluoromethyl, carboxy, tetrazolyl, —$SO_2$H, $C_1$-$C_6$ alkyl-C(O)—NH—, $C_1$-$C_6$ alkyl-$SO_2$—NH—, and $C_1$-$C_6$ alkyl-SO—NH—; and (ii) 5- to 6-membered heterocyclyl containing 1 to 3 heteroatoms selected from the group consisting of N, O, S, and $S(O)_2$ wherein said heterocyclyl of $R^1$ is unsubstituted or substituted with one to two moieties independently selected from the group consisting of halo, $C_1$-$C_6$ alkyl, $C_1$-$C_6$ alkoxy, cyano, hydroxy, amino, $C_1$-$C_6$ alkylamino, and $C_1$-$C_6$ dialkylamino.

6. The compound of claim 1, wherein $R^6$ is H or $C_1$-$C_6$alkyl and $R^7$ is H or $C_1$-$C_6$alkyl.

7. The compound of claim 1, wherein $R^3$ is a 5- to 6-membered heteroaryl or phenyl unsubstituted or substituted with one to three moieties, which can be the same or different, each moiety being selected from the group consisting of halogen, $C_1$-$C_6$alkyl, phenyl, 5- to 6-membered heteroaryl, —$CF_3$, —CN, —C(O)OH, —$(CR^aR^b)_n$C(O)OH, —$OCF_3$, —O-halo$C_1$-$C_6$alkyl, —$OR^a$, —$C(O)R^a$, —$NR^aR^b$, —C(O)O—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$, wherein the alkyl, phenyl or heteroaryl is optionally substituted with one to three moieties, which can be the same or different, each moiety being selected from the group consisting of halogen, $C_1$-$C_6$alkyl, —$CF_3$, —CN, -C(O)OH, —$(CR^aR^b)_n$C(O)OH, —$OCF_3$, —O-halo$C_1$-$C_6$alkyl, —$OR^a$, —$C(O)R^a$, —$NR^aR^b$, —C(O)O—$C_1$-$C_6$alkyl, -$C(O)NR^aR^b$, —$NR^aC(O)R^b$, —$S(O_2)NR^aR^b$, —$NR^aS(O_2)R^b$, —$SR^a$, and —$S(O_2)R^a$;

Wherein all other substituents are as defined in claim 1.

8. The compound of claim 7, wherein $R^3$ is pyrazolyl, isoquinolinyl, pyrimidinyl, phenyl or pyridyl, unsubstituted or substituted with one to three moieties, which can be the same or different, each moiety being selected from the group consisting of halogen, $C_1$-$C_6$alkyl, phenyl, 5- to 6-membered heteroaryl, —$CF_3$, —CN, —C(O)OH, —$(CR^aR^b)$C(O)OH, —$OCF_3$, —O-halo$C_1$-$C_6$alkyl, —$OR^a$, —$C(O)R^a$, —$NR^aR^b$, —C(O)O—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$, wherein the alkyl, phenyl or heteroaryl is optionally substituted with one to three moieties, which can be the same or different, each moiety being selected from the group consisting of halogen, $C_1$-$C_6$alkyl, —$CF_3$, —CN, —C(O)OH, —$(CR^aR^b)_N$C(O)OH, —$OCF_3$, —O-halo$C_1$-$C_6$alkyl, —$OR^a$, —$C(O)R^a$, —$NR^aR^b$, —C(O)O—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$.

9. The compound of claim 8, wherein $R^3$ is

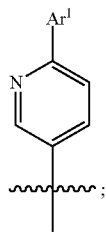

$Ar^1$ is phenyl or a 5- to 6-membered heteroaryl optionally substituted with one to three of $R^{12}$, which can be the same or different, each $R^{12}$ being selected from the group consisting of halogen, $C_1$-$C_6$alkyl, —$CF_3$, —CN, —C(O)OH, —$(CR^aR^b)_n$C(O)OH, —$OCF_3$, —O-halo$C_1$-$C_6$alkyl, —$OR^a$, —$C(O)R^a$, —$NR^aR^b$, —C(O)O—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$.

10. The compound of claim 9 wherein $Ar^1$ is phenyl, pyridyl, pyrimidinyl, imidazolyl, pyrazinyl, pyrazolyl, or thiazolyl, optionally substituted with one to three of $R^{12}$, which can be the same or different, each $R^{12}$ being selected from the group consisting of halogen, $C_1$-$C_6$alkyl, —$CF_3$, —CN, —C(O)OH, —$(CR^aR^b)_n$C(O)OH, —$OCF_3$, —O-halo$C_1$-$C_6$alkyl, —$OR^a$, —$C(O)R^a$, —$NR^aR^b$, —C(O)O—$C_1$-$C_6$alkyl, —$C(O)NR^aR^b$, —$NR^aC(O)R^b$, —$S(O_2)NR^aR^b$, —$NR^aS(O_2)R^b$, —$SR^a$, and —$S(O_2)R^a$.

11. The compound of claim 9, wherein $R^{12}$ is selected from the group consisting of halogen, $C_1$-$C_6$alkyl, —$CF_3$, and —$OCF_3$.

12. A compound selected from the group consisting of:

((1R,3s,5S)-3-(3-methyl-6-(6-phenylpyridin-3-yl)-1H-dipyrazolo[1,5-a:4',3'-e]pyrimidin-4-yl)-8-azabicyclo[3.2.1]octan-8-yl)(4H-1,2,4-triazol-3-yl)methanone;

((1R,3s,5S)-3-(3-(6-phenylpyridin-3-yl)-8H-pyrazolo[1,5-a]pyrrolo[3,2-e]pyrimidin-5-yl)-8-azabicyclo[3.2.1]octan-8-yl)(4H-1,2,4-triazol-3-yl)methanone;

((1R,3s,5S)-3-(3-(6-(2-hydroxypropan-2-yl)pyridin-3-yl)-8H-pyrazolo[1,5-a]pyrrolo[3,2-e]pyrimidin-5 -yl)-8-azabicyclo [3.2.1]octan-8-yl)(1H-1,2,4-triazol-3 -yl)methanone;

2-hydroxy-1-((lR,3s,5S)-3-(3-(6-(2-hydroxypropan-2-yl)pyridin-3-yl)-8H-pyrazolo[1,5-a]pyrrolo[3,2-e]pyrimidin-5-yl)-8-azabicyclo[3.2.1]octan-8-yl)ethanone;

((1R,3s,5S)-3-(3-(6-(1H-imidazol-2-yl)pyridin-3-yl)-8H-pyrazolo[1,5-a]pyrrolo[3,2-e]pyrimidin-5-yl)-8-azabicyclo[3.2.1]octan-8-yl)-2-hydroxyethanone; and ((1R,3s,5S)-3-(3-(6-(1H-imidazol-2-yl)pyridin-3-yl)-8H-pyrazolo[1,5-a]pyrrolo[3,2-e]pyrimidin-5-yl)-8-azabicyclo[3.2.1]octan-8-yl)(4H-1,2,4-triazol-3-yl)methanone;

Or a stereoisomer thereof

Or a pharmaceutically acceptable salt thereof

Or a pharmaceutically acceptable salt of the stereoisomer thereof.

13. A pharmaceutical composition comprising a therapeutically effective amount of the compound of claims 1 and a pharmaceutically acceptable carrier and optionally other therapeutic ingredients.

* * * * *